US008044200B2

(12) United States Patent
Xu et al.

(10) Patent No.: US 8,044,200 B2
(45) Date of Patent: Oct. 25, 2011

(54) SYNTHESIS AND PURIFICATION OF PTEROIC ACID AND CONJUGATES THEREOF

(75) Inventors: Le-Cun Xu, West Lafayette, IN (US); Iontcho Radoslavov Vlahov, West Lafayette, IN (US); Christopher Paul Leamon, West Lafayette, IN (US); Hari Krishna Santhapuram, West Lafayette, IN (US); Chunhong Li, Bear, DE (US)

(73) Assignee: Endocyte, Inc., West Lafayette, IN (US)

( * ) Notice: Subject to any disclaimer, the term of this patent is extended or adjusted under 35 U.S.C. 154(b) by 25 days.

(21) Appl. No.: 11/908,695

(22) PCT Filed: Mar. 14, 2006

(86) PCT No.: PCT/US2006/009153
§ 371 (c)(1),
(2), (4) Date: Sep. 14, 2007

(87) PCT Pub. No.: WO2006/101845
PCT Pub. Date: Sep. 28, 2006

(65) Prior Publication Data
US 2008/0207625 A1    Aug. 28, 2008

Related U.S. Application Data

(60) Provisional application No. 60/662,277, filed on Mar. 16, 2005.

(51) Int. Cl.
C07D 475/04    (2006.01)
A61P 35/00    (2006.01)

(52) U.S. Cl. ...................................... 544/258
(58) Field of Classification Search .................. 544/238, 544/258
See application file for complete search history.

(56) References Cited

U.S. PATENT DOCUMENTS

| 2,515,483 | A | 7/1950 | Wolf et al. |
|---|---|---|---|
| 2,816,110 | A | 12/1957 | Sletzinger et al. |
| 3,387,001 | A | 6/1968 | Hargrove et al. |
| 3,392,173 | A | 7/1968 | Hargrove et al. |
| 4,166,810 | A | 9/1979 | Cullinan et al. |
| 4,203,898 | A | 5/1980 | Cullinan et al. |
| 4,316,885 | A | 2/1982 | Rakhit |
| 4,337,339 | A | 6/1982 | Farina et al. |
| 4,639,456 | A | 1/1987 | Trouet et al. |
| 4,650,803 | A | 3/1987 | Stella et al. |
| 4,691,024 | A | 9/1987 | Sirahata |
| 4,713,249 | A | 12/1987 | Schroder |
| 4,801,688 | A | 1/1989 | Laguzza et al. |
| 4,866,180 | A | 9/1989 | Vyas et al. |
| 5,006,652 | A | 4/1991 | Cullinan et al. |
| 5,094,849 | A | 3/1992 | Cullinan et al. |
| 5,100,883 | A | 3/1992 | Schiehser |
| 5,108,921 | A | 4/1992 | Low et al. |
| 5,118,677 | A | 6/1992 | Caufield |
| 5,118,678 | A | 6/1992 | Kao et al. |
| 5,120,842 | A | 6/1992 | Failli et al. |
| 5,130,307 | A | 7/1992 | Failli et al. |
| 5,138,051 | A | 8/1992 | Hughes et al. |
| 5,140,104 | A | 8/1992 | Coughlin et al. |
| 5,151,413 | A | 9/1992 | Caufield et al. |
| 5,169,851 | A | 12/1992 | Hughes et al. |
| 5,194,447 | A | 3/1993 | Kao |
| 5,221,670 | A | 6/1993 | Caufield |
| 5,233,036 | A | 8/1993 | Hughes |
| 5,258,389 | A | 11/1993 | Goulet et al. |
| 5,260,300 | A | 11/1993 | Hu |
| 5,266,333 | A | 11/1993 | Cady |
| 5,302,584 | A | 4/1994 | Kao et al. |
| 5,362,718 | A | 11/1994 | Skotnicki et al. |
| 5,378,696 | A | 1/1995 | Caufield |
| 5,385,908 | A | 1/1995 | Nelson et al. |
| 5,385,909 | A | 1/1995 | Nelson et al. |
| 5,385,910 | A | 1/1995 | Ocain et al. |
| 5,389,639 | A | 2/1995 | Failli et al. |
| 5,391,730 | A | 2/1995 | Skotnicki et al. |
| 5,416,016 | A | 5/1995 | Low et al. |
| 5,417,982 | A | 5/1995 | Modi |
| 5,463,048 | A | 10/1995 | Skotnicki et al. |
| 5,491,231 | A | 2/1996 | Nelson et al. |
| 5,547,668 | A | 8/1996 | Kranz et al. |
| 5,552,545 | A | 9/1996 | Pearce et al. |
| 5,627,165 | A | 5/1997 | Glazier |
| 5,635,382 | A | 6/1997 | Low et al. |
| 5,672,486 | A | 9/1997 | Soulillou |
| 5,688,488 | A | 11/1997 | Low et al. |
| 5,998,603 | A | 12/1999 | Cook |
| 6,004,555 | A | 12/1999 | Thorpe et al. |
| 6,030,941 | A | 2/2000 | Summerton et al. |
| 6,056,973 | A | 5/2000 | Allen |
| 6,077,499 | A | 6/2000 | Griffiths |
| 6,093,382 | A | 7/2000 | Wedeking et al. |
| 6,171,614 | B1 | 1/2001 | Chaikof et al. |
| 6,171,859 | B1 | 1/2001 | Herrnstadt et al. |
| 6,177,404 | B1 | 1/2001 | DeFeo-Jones et al. |
| 6,184,042 | B1 | 2/2001 | Neumann et al. |
| 6,207,157 | B1 | 3/2001 | Gu et al. |
| 6,291,673 | B1 | 9/2001 | Fuchs et al. |

(Continued)

FOREIGN PATENT DOCUMENTS

CA    2372841    11/2000

(Continued)

OTHER PUBLICATIONS

Prabhu, et al., Phytochem., vol. 45, # 1, May 1997, pp. 23-27.*

(Continued)

*Primary Examiner* — James O Wilson
*Assistant Examiner* — Cecilia M Jaisle
(74) *Attorney, Agent, or Firm* — Barnes & Thornburg LLP

(57) ABSTRACT

Methods for purifying pteroic acid, analogs of pteroic acid, and derivatives of pteroic acid are described. Methods for synthesizing and purifying conjugates of vitamins, including FITC conjugates of folic acid, folic acid analogs, and derivatives of folic acid and folic acid analogs are also described. Purified forms of pteroic acid, derivatives and analogs of pteroic acid, and conjugates thereof are also described.

21 Claims, 2 Drawing Sheets

U.S. PATENT DOCUMENTS

| | | |
|---|---|---|
| 6,291,684 B1 | 9/2001 | Borzilleri et al. |
| 6,335,434 B1 | 1/2002 | Guzaev et al. |
| 6,365,179 B1 | 4/2002 | Zalipsky et al. |
| 6,399,625 B1 | 6/2002 | Zhu |
| 6,399,626 B1 | 6/2002 | Zhu et al. |
| 6,399,638 B1 | 6/2002 | Vite et al. |
| 6,432,973 B1 | 8/2002 | Zhu et al. |
| 6,440,991 B1 | 8/2002 | Zhu et al. |
| 6,511,986 B2 | 1/2003 | Zhang et al. |
| 6,541,612 B2 | 4/2003 | Mulnar-Kimber et al. |
| 6,596,757 B1 | 7/2003 | Chari et al. |
| 6,617,333 B2 | 9/2003 | Raibindran et al. |
| 6,670,355 B2 | 12/2003 | Azrulan et al. |
| 6,677,357 B2 | 1/2004 | Zhu et al. |
| 6,680,330 B2 | 1/2004 | Fawzi et al. |
| 6,713,607 B2 | 3/2004 | Caggiano et al. |
| 6,800,653 B2 | 10/2004 | Regueiro-Ren et al. |
| 6,821,731 B2 | 11/2004 | Gillis et al. |
| 6,915,855 B2 | 7/2005 | Steele et al. |
| 6,958,153 B1 | 10/2005 | Ormerod et al. |
| 7,019,014 B2 | 3/2006 | Bernan et al. |
| 7,029,674 B2 | 4/2006 | Carreno et al. |
| 7,033,594 B2 | 4/2006 | Low et al. |
| 7,060,709 B2 | 6/2006 | Cooperstone et al. |
| 7,060,797 B2 | 6/2006 | O'Toole et al. |
| 7,067,111 B1 | 6/2006 | Yang et al. |
| 7,074,804 B2 | 7/2006 | Zhu et al. |
| 7,105,328 B2 | 9/2006 | Wood et al. |
| 7,122,361 B2 | 10/2006 | Liu et al. |
| 7,128,893 B2 | 10/2006 | Leamon et al. |
| 7,153,957 B2 | 12/2006 | Chew et al. |
| 7,601,332 B2 | 10/2009 | Vlahov et al. |
| 2003/0086900 A1 | 5/2003 | Low et al. |
| 2003/0162234 A1 | 8/2003 | Jallad |
| 2004/0018203 A1 | 1/2004 | Pastan et al. |
| 2004/0033195 A1 | 2/2004 | Leamon et al. |
| 2004/0242582 A1 | 12/2004 | Green et al. |
| 2005/0004010 A1 | 1/2005 | Collins et al. |
| 2005/0026068 A1 | 2/2005 | Gogolides et al. |
| 2005/0107325 A1 | 5/2005 | Mancharan et al. |
| 2005/0165227 A1 | 7/2005 | Vlahov et al. |
| 2005/0227985 A9 | 10/2005 | Green et al. |
| 2005/0239713 A1 | 10/2005 | Domling et al. |
| 2005/0239739 A1 | 10/2005 | Matulic-Adamic et al. |
| 2006/0058266 A1 | 3/2006 | Manoharan et al. |
| 2006/0128754 A1 | 6/2006 | Hoefle et al. |
| 2007/0009434 A1 | 1/2007 | Low et al. |
| 2007/0275904 A1 | 11/2007 | Vite et al. |
| 2008/0207625 A1 | 8/2008 | Xu et al. |
| 2008/0248052 A1 | 10/2008 | Vlahov et al. |
| 2008/0280937 A1 | 11/2008 | Leamon et al. |
| 2009/0203889 A1 | 8/2009 | Vlahov et al. |
| 2010/0004276 A1 | 1/2010 | Vlahov et al. |
| 2010/0048490 A1 | 2/2010 | Vlahov et al. |
| 2010/0104626 A1 | 4/2010 | Leamon et al. |

FOREIGN PATENT DOCUMENTS

| | | |
|---|---|---|
| CA | 2376175 | 12/2000 |
| EP | 0 116 208 A1 | 8/1984 |
| EP | 0 163 550 A2 | 12/1985 |
| EP | 0 247 792 | 12/1987 |
| EP | 0 280 741 A1 | 9/1988 |
| EP | 0 354 728 | 2/1990 |
| JP | 59-175493 | 10/1984 |
| JP | 60-255789 | 12/1985 |
| WO | WO 88/01622 | 3/1988 |
| WO | WO 90/12096 | 10/1990 |
| WO | WO 91/07418 | 5/1991 |
| WO | WO96/36367 | 11/1996 |
| WO | WO 98/10651 A1 | 3/1998 |
| WO | WO 99/20626 A1 | 4/1999 |
| WO | WO 99/61055 | 12/1999 |
| WO | WO 00/35422 | 6/2000 |
| WO | WO 00/66091 | 11/2000 |
| WO | WO 00/74721 | 12/2000 |
| WO | WO 01/28592 | 4/2001 |
| WO | WO 01/74382 | 10/2001 |
| WO | WO 02/085908 | 10/2002 |
| WO | WO 02/087424 | 11/2002 |
| WO | WO 02/098868 | 12/2002 |
| WO | WO 03/097647 | 11/2003 |
| WO | WO 2004/005326 | 1/2004 |
| WO | WO 2004/005327 | 1/2004 |
| WO | WO 2004/012735 | 2/2004 |
| WO | WO 2004/046170 | 6/2004 |
| WO | WO 2004/054622 | 7/2004 |
| WO | WO 2004/069159 | 8/2004 |
| WO | WO2004/100983 | 11/2004 |
| WO | WO 2005/074901 | 8/2005 |
| WO | WO 2005/112919 | 12/2005 |
| WO | WO 2006/012527 | 2/2006 |
| WO | WO 2006/042146 | 4/2006 |
| WO | WO 2006/101845 | 9/2006 |
| WO | WO2006/105141 | 10/2006 |
| WO | WO 2007/022493 | 2/2007 |
| WO | WO 2007/022494 | 2/2007 |
| WO | WO 2008/101231 | 8/2008 |
| WO | WO 2008/112873 | 9/2008 |
| WO | WO 2009/002993 | 12/2008 |
| WO | WO 2009/055562 | 4/2009 |

OTHER PUBLICATIONS

Wikipedia, Derivative (Chemistry), http://en.wikipedia.org/wiki/Derivative_(chemistry), downloaded Dec. 16, 2009.*

Wikipedia, Analog (Chemistry), http://en.wikipedia.org/wiki/Analog_(chemistry), downloaded Dec. 16, 2009.*

Wikipedia, List of Purification Methods in Chemistry, http://en.wikipedia.org/wiki/List_of_purification_methods_in_chemistry, downloaded Dec. 16, 2009.*

Wikipedia, Solution, http://en.wikipedia.org/wiki/Solution, downloaded Dec. 17, 2009.*

Principles of Ion Exchange Chromatography, http://www.separations.us.tosohbioscience.com/ServiceSupport/TechSupport/ResourceCenter/PrinciplesofChromatography/Ion Exchange, downloaded Dec. 23, 2009.*

Wikipedia, Conjugate, http://en.wikipedia.org/wiki/Conjugate, downloaded Dec. 17, 2009.*

Wikipedia, Complex (Chemistry), http://en.wikipedia.org/wiki/Complex_(chemistry), downloaded Dec. 23, 2009.*

Wikipedia, List of Purification Methods in Chemistry, http://en.wikipedia.org/wiki/List_of_purification_methods_in_chemistry, downloaded Dec. 16, 2009.*

Wikipedia, Solution, http://en.wikipedia.org/wiki/Solution, downloaded Dec. 17, 2009.*

Bartels, et al., J. Chromatog. A, vol. 659, #1, Jan. 21, 1994, pp. 185-189.*

Nomura, Makoto, et al., "Development of an Efficient Intermediate α-[2-(Trimethylsily1)ethoxy]-2-N-[2-(trimethylsily1)ethoxycarbony1]folic Acid, for the Synthesis of Folate (γ)-Conjugates, and Its Application to the Synthesis of Folate-Nucleoside Congugates," *Journal of Organic Chemistry*, 2000, vol. 65, pp. 5016-5021.

Harvison, Peter J., et al., "Synthesis and Biological Activity of Novel Folic Acid Analogues: Pteroyl-S-alkylhomocysteine Sulfoximines," *Journal of Medicinal Chemistry*, 1992, vol. 35, pp. 1227-1233.

Scott, John M, "Preparation and Purification of Pteroic Acid from Pteroylglutamic Acid (Folic Acid)," *Methods In Enzymology*, 1980, vol. 66, pp. 657-660.

Archer, Michael C., et al., "Separation of Folic Acid Derivatives and Pterins by High-Performance Liquid Chromatography," *Methods In Enzymology*, 1980, vol. 66, pp. 452-459.

Houlihan, Catherine M., et al., "Preparation and Purification of Pteroic Acid from Folic Acid," *Analytical Biochemistry*, 1972, vol. 46, pp. 1-6.

Lemon, Julia, et al., "Conversion of Pterolyglutamic Acid To Pteroic Acid By Bacterial Degradation," *Archives of Biochemistry*, 1948, vol. 19, pp. 311-316.

Levy, Carl C., et al. "The Enzymatic Hydrolysis Of Methotrexate And Folic Acid", 1967, *The Journal Of Biological Chemistry*, vol. 242, No. 12, pp. 2933-2938.

Pratt, Alan G., et al. "The Hydrolysis Of Mono-, Di, And Triglutamate Derivatives Of Folic Acid With Bacterial Enzymes", 1968, *The Journal Of Biological Chemistry*, vol. 243, No. 24, pp. 6367-6372.

Angier, R. B., et al., "Pteroic Acid Analogs Containing Arsenic," Notes, vol. 76, 1954, pp. 902-904.

Boothe, J. H., et al., "Pteroic Acid Derivatives. II. Pteroyl-γ-glutamylglutamic Acid and Pteroyl-γ-glutamyl-γ-glutamylglutamic Acid," Pteroic Acid Derivatives, vol. 70, 1948, pp. 1099-1102.

Agoston E.S. et al., "Vitamin D Analogs as Anti-Carcinogenic Agents," *Anti-Cancer Agents in Medicinal Chemistry*, 2006; 6(1): 53-71.

Anderson et al., "Potocytosis: Sequestration and transport of small molecules by caveolae," *Science*, 1992; 255: 410-411.

Antony A.C., "Folate receptors," *Annu Rev Nutr*, 1996; 16: 501-21.

Antony A.C., "The biological chemistry of folate receptors," *Blood*, 1992; 79(11):2807-2820.

Antony A.C. et al., "Studies of the Role of a Particulate Folate-binding Protein in the Uptake of 5-Methyltetrahydrofolate by Cultured Human KB Cells," *J. Biological Chem.*, 1985; 260(28):14911-7.

Arya et al., "Design and Synthesis of Analogs of Vitamin E: Antiproliferative Activity Against Human Breast Adenocarcinoma Cells," *Bioorganic & Medicinal Chemistry Letters*, 1998; vol. 8, pp. 2433-2438.

Ayers W.A., "Effect of Vitamin B12 and Analogs on the Respiration of a Marine Bacterium," *Archives of Biochemistry and Biophysics*, 1962, vol. 96, pp. 210-215.

Barnett C.J. et al., "Structure-Activity Relationships of Dimeric Catharanthus Alkaloids. 1. Deacetylvinblastine Amide (Vindesine) Sulfate," *J. Med. Chem.* 21: 88-96 (1978).

Bavetsias, V. et al., "Design and synthesis of Cyclopenta[g]quinazoline-based antifolates as inhibitors of thymidylate synthase and potential antitumor agents," J Med Chem, 2000; 43(10): 1910-1926.

Bavetsias, V., et al., "The design and synthesis of water-soluble analogues of CB30865, a quinazolin-4-one-based antitumor agent," J Med Chem, 2002; 45(17): 3692-3702.

Bock et al., "Sulfonamide structure-activity relationships in a cell-free system. 2. Proof for the formation of a sulfonamide-containing folate analog," *Journal of Medical Chemistry*, 17: 23-28 (1974).

Boger, D.L. et al., "An improved synthesis of 1,2,9,9a-tetrahydrocyclopropa[c]benz[e]indol-4-one (CBI): a simplified analog of the CC-1065 alkylation subunit," *J. Org. Chem.*, 1992; 57: 2873-2876.

Campbell et al., "Folate-binding protein is a marker for ovarian cancer," *Cancer Res.*, 1991; 51: 5329-5338.

Cho et al., "Single-chain Fv/folate conjugates mediate efficient lysis of folate-receptor-positive tumor cells," *Bioconjug. Chem.* 8(3): 338-346 (1997).

Christensen et al., "Membrane receptors for endocytosis in the renal proximal tubule," *Int. Rev. Cytol.*, 1998; 180: 237-284.

Churlaud C. et al., "Novel 4-(Trimethylsilyl)aminoalkanes and 4-(Trimethylsilyl)aminoalk-2-enes, via a 1,5-Hydride Shift, in the Reaction of α-Unsaturated Silanes with Aminomethylbenzotriazoles," *Organomettalics*, 1999; 18(21): 4270-4274.

Citro G. et al., "Inhibition of leukemia cell proliferation by folic acid—polylysine-mediated introduction of c-*myb* antisense oligodeoxynucelotides into IIL-60 cells," *Br. J. Cancer*, 1994; 69: 463-467.

Cope A.C. et al., "Thermal Rearrangement of Allyl-type Sulfoxides, Sulfones and Sulfinates," *J. Am. Chem. Soc.*, 1950; 72; 59-67.

DeVita, Jr., Vincent et al (eds); *Biologic Therapy of Cancer*; 2nd ed., J.B. Lippincott Company; 1995.

Domling A. et al., "Myxobacterial Epothilones and Tubulysins as Promising Anticancer Agents," *Molecular Diversity*, 2005; 9: 141-147.

Douglas J.T. et al., "Targeted Gene Delivery by Tropism-Modified Adenoviral Vectors," *Nat. Biotechnol.*, 1996, vol. 14, pp. 1574-1578.

Eichman, J.D. et al., "The Use Of PAMAM Dendrimers In The Efficient Transfer Of Genetic Material Into Cells", Jul. 2000, *PSTT*, vol. 3, No. 7, pp. 232-245.

Foong, L.Y. et al., "Development of a Novel Thiol Reagent for Probing Ion Channel Structure: Studies in a Model System," Biochemistry, 1997, vol. 36, pp. 1343-1348.

Frankel AE., "Immunotoxin therapy of cancer," *Oncology*, 1993; 7(5): 69-78.

Shealy Y.F., "Synthesis and Evaluation of Some New Retinoids for Cancer Chemoprevention," *Preventive Medicine*, 1989, vol. 18, pp. 624-645.

Gangjee et al., "The effect of 5-alkyl modification on the biological activity of pyrrolo[2,3-d]pyrimidine containing classical and non-classical antifolates as inhibitors of dihydrofolate reductase and as antitumor and/or antiopportunistic infection agents," *J Med Chem.*, 2008; 51(15):4589-4600.

Garin-Chesa et al., "Trophoblast and ovarian cancer antigen LK26. Sensitivity and specificity in immunopathology and molecular identification as a folate-binding protein," *Am. J. Pathol.* 142(2): 557-562 (1993).

Gibbs, DD et al., "BGC 945, a novel tumor-selective thymidylate synthase inhibitor targeted to alpha-folate receptor-overexpressing tumors," Cancer Res, 2005; 65(24): 11721-11728.

Gottschalk S. et al., "Folate receptor mediated DNA delivery into tumor cells: potosomal disruption results in enhanced gene expression," *Gene Therapy*, 1994; 1(3): 185-191.

Greene T.E. et al., "Protective Groups in Organic Synthesis," 2d edition, John Wiley & Sons, Inc. New York (1991).

Hanck A.B. et al., "Dexpanthenol (Ro 01-4709) in the treatment of constipation," *Acta Vitaminol Enzymol*, 1982; vol. 4 (1-2), pp. 87-97 (abstract only).

Henderson, E.A. et al., Targeting the alpha-folate receptor with cyclopenta[g]quinazoline-based inhibitors of thymidylate synthase, Bioorg Med Chem, 2006; 14(14): 5020-5042.

U.S. Appl. No. 60/946,092, filed Jun. 25, 2007, Vlahov et al.
U.S. Appl. No. 60/982,595, filed Oct. 25, 2007, Vlahov et al.
U.S. Appl. No. 61/036,176, filed Mar. 13, 2008, Vlahov et al.
U.S. Appl. No. 61/036,186, filed Mar. 13, 2008, Vlahov et al.
U.S. Appl. No. 12/739,579, filed Apr. 23, 2010, Vlahov et al.

Hofland et al., "Folate-targeted gene transfer in vivo," *Mol Ther* 5(6): 739-744 (2002).

Hofle, G. et al., "Semisynthesis and Degradation of the Tubulin Inhibitors Epothilone and Tubulysin", 2003, *Pure Appl. Chem.*, vol. 75, Nos. 2-3, pp. 167-178.

Holladay et al., "Riboflavin-mediated delivery of a macromolecule into cultured human cells," *Biochim Biophys Acta*, 1426(1): 195-204 (1999).

Holm, J. et al., "Folate receptors in malignant and benign tissues of human female genital tract," *BioSci. Rep.*, 17(4): 415-427 (1997).

Holm, J. et al., "High-affinity folate binding in human choroid plexus. Characterization of radioligand binding, immunoreactivity, molecular heterogeneity and hydrophobic domain of the binding protein," *Biochem J.*, 280(1): 267-271 (1991).

Hosomi A. et al., "Affinity for a-tocopherol transfer protein as a determinant of the biological activities of vitamin E analogs," *Federation of European Biochemical Societies Letters*, 1997, vol. 409, pp. 105-108.

Hynes et al., "Quinazolines as inhibitors of dihydrofolate reductase. 4. Classical analogues of folic and isofolic acids", *Journal of Medical Chemistry*, 1977; 20: 588-591.

Jackman, A. L. et al., "Antifolates targeted specifically to the folate receptor," Adv Drug Deliv Rev, 2004; 56(8): 1111-1125.

U.S. Appl. No. 12/775,824, filed May 7, 2010, Green et al.
U.S. Appl. No. 12/666,712, filed Dec. 24, 2009, Leamon et al.

Jones T.R. et al., "A potent antitumour quinazoline inhibitor of thymidylate synthetase: synthesis, biological properties and therapeutic results in mice," *Eur J Cancer*, 1981; 17(1):11-9.

Jones T.R. et al., "Quinazoline antifolates inhibiting thymidylate synthase: variation of the amino acid," *J Med Chem*, 1986; 29(6):1114-8.

Jung K.H. et al., "Intramolecular o-glycoside bond formation," *Chem. Rev.*, 2000, 100, 4423-42.

Kagechika H et al., "Synthetic Retinoids: Recent Developments Concerning Structure and Clinical Utility," *Journal of Medicinal Chemistry*, 2005; vol. 48, No. 19, pp. 5875-5883.

Kamen et al., "Delivery of folates to the cytoplasm fo MA104 cells is mediated by a surface receptor that recycles," *J. Biol. Chem.*, 263: 13602-13609 (1988).

Kamen et al., "The folate receptor works in tandem with a probenecid-sensitive carrier in MA104 cells in vitro," *J. Clin. Invest.*, 87(4): 1442-1449 (1991).

Kamen, B. A. et al., "Receptor-mediated folate accumulation is regulated by the cellular folate content," *Proc. Natl. Acad. Sci.* USA, 83: 5983-5987 (1986).

Kandiko C.T. et al., "Inhibition of Rat Brain Pyruvate Dehydrogenase by Thiamine Analogs," *Biochemical Pharmacology*, 1988; vol. 37, No. 22, pp. 4375-4380.

Kane et al., "The influence of extracellular folate concentration on methotrexate uptake by human KB cells. Partial characterization of a membrane-associated methotrexate binding protein," *J. Biol. Chem.*, 261: 44-49 (1986).

Kranz et al., "Conjugates of folate and anti-T-cell-receptor antibodies specifically target folate-receptor-positive tumor cells for lysis," *Proc. Natl. Acad. Sci.* USA, 1995; 92(20), pp. 9057-9061.

Kumar H.P. et al., "Folate transport in *Lactobacillus salivarius*. Characterization of the transport mechanism and purification and properties of the binding component," *J. Biol. Chem.*. 1987; 262(15):7171-7179.

Ladino et al., "Folate-maytansinoids: target-selective drugs of low molecular weight," *Int. J. Cancer*, 73(6): 859 864 (1997).

Lambooy J. P., "Riboflavin Analogs Utilized for Metabolism by a Lactobacillus Casei Mutant," *Int. J. Biochem.*, vol. 16, No. 2, 1984, pp. 231-234.

Landuer W. et al., "The Interaction in Teratogenic Activity of the Two Niacin Analogs 3-acetylpyridine and 6-aminonicotinamide," *J Exp Zool*, 151(3):253-258 (1962).

Langone, J.J., et al., "Radioimmunoassays For The Vinca Alkaloids, Vinblastine And Vincristine", 1979, *Analytical Biochemistry*, No. 95, pp. 214-221.

Larock R.C., "Comprehensive Organic Transformations, a guide to functional group preparations," VCH Publishers, Inc. New York (1989).

Leamon CP et al, "Cytotoxicity of folate-Pseudomonas exotoxin conjugates toward tumor cells. Contribution of translocation domain," *J. Biol. Chem*. 268(33): 24847-24854 (1993).

Leamon CP et al., "Comparative Preclinical Activity of the Folate-targeted Vinca Alkaloid Conjugates EC140 and EC145," *Int J Cancer*, 2007; 121(7):1585-92.

Leamon CP et al., "Cytotoxicity of momordin-folate conjugates in cultured human cells," *J. Biol. Chem.*, 1992; 267(35): 24966-24971.

Leamon CP et al., "Delivery of macromolecules into living cells: a method that exploits folate receptor endocytosis," *Proc. Natl. Acad. Sci.* USA 88(13): 5572-5573 (1991).

Leamon CP et al., "Folate-mediated targeting: from diagnostics to drug and gene delivery," *Drug Discovery Today* 6: 36-43 (2001).

Leamon CP et al., "Folate-targeted chemotherapy," *Adv Drug Deliv Rev*, 2004;56(8): 1127-41.

Leamon CP et al., "Membrane folate-binding proteins are responsible for folate-protein conjugate endocytosis into cultured cells," *Biochem. J*. 291: 855-860 (1993).

Leamon CP et al., "Selective targeting of malignant cells with cytotoxin-folate conjugates," *J. Drug Target*. 2(2): 101-112 (1994). U.S. Appl. No. 60/590,580, filed Jul. 23, 2004, Vlahov et al.

Leamon CP et al., "Synthesis and biological evaluation of EC140: A novel folate-targeted vinca alkaloid conjugate," *Bioconjug Chem*, 2006;17(5):1226-32.

Leamon CP et al., "Synthesis and Biological Evaluation of EC20: A New Folate-Derived, (99m)Tc-Based Radiopharmaceutical," *Bioconjug. Chem*. 13(6): 1200-1210 (2002).

Leamon CP et al., "Synthesis and biological evaluation of EC72: a new folate-targeted chemotherapeutic," *Bioconjug Chem.*, 2005;16(4):803-11.

Leamon et al., "Folate-mediated drug delivery: effect of alternative conjugation chemistry," *J. Drug Target* 7(3): 157-169 (1999).

Lee et al, "Measurement of Endosome pH Following Folate Receptor-Mediated Endocytosis," *Biochim. Biophys.* Acta 1312(3): 237-242 (1996).

Lee W.W. et al., "Folic acid antagonists. Methotrexate analogs containing spurious amino acids. Dichlorohomofolic acid," *Journal of Medical Chemistry*, 17: 326-330 (1974).

Lee et al., "Synthesis and evaluation of taxol-folic acid conjugates as targeted antineoplastics," *Bioorg Med Chem*. 10(7): 2397-2414, (2002).

Lee, Francis Y. F., et al., "BMS-247550: A Novel Epothilone Analog With A Mode Of Action Similar To Paclitaxel But Possessing Superior Antitumor Efficacy," *Clin Cancer Res*, 2001, No. 7, pp. 1429-1437.

Lee, R. J. and Huang, L., "Folate-Targeted, Anionic Liposome-Entrapped Polylysine-Condensed Dna For Tumor Cell-Specific Gene Transfer," *J. Biol. Chem.* 271(14): 8481-8487 (1996).

Lee, R. J. and Low, P. S, "Delivery of liposomes into cultured KB cells via folate receptor-mediated endocytosis," *J. Biol. Chem.* 269(5): 3198-3204 (1994).

Lee, R. J. and Low, P. S., "Folate-mediated tumor cell targeting of liposome-entrapped doxorubicin in vitro," *Biochim. Biophys.* Acta 1233: 134-144 (1995).

Lewis et al., "Receptor-mediated folate uptake is positively regulated by disruption of actin cytoskeleton," *Cancer Res*. 58(14): 2952-2956 (1998).

Li et al, "Targeted delivery of antisense oligodeoxynucleotides by LPDII," *J. Liposome Res*. 7(1): 63 (1997).

Liu et al., "Targeted Drug Delivery to Chemoresistant Cells: Folic Acid Derivatization of FdUMP[10] Enhances Cytotoxicity Toward 5-FU-Resistant Human Colorectal Tumor Cells," *J. Org. Chem*. 66: 5655-5663 (2001).

Lonsdale D, "A Review of the Biochemistry, Metabolism and Clinical Benefits of Thiamin(e) and Its Derivatives," publication, Advance Access Publication, vol. 3, Feb. 2006, pp. 49-59.

Lopes et al., "Acyloxymethyl as a drug protecting group. Part 5.1 Kinetics and mechanism of the hydrolysis of tertiary N-acyloxymethylsulfonamides," *J. Chem. Soc*., Perkin Trans. 2, pp. 431-439 (1999).

Low P.S. et al., "Folate Receptor-Targeted Drugs for Cancer and Inflammatory Diseases," *Adv Drug Deliv Rev*, 2004;56(8):1055-238.

Lu et al., "Folate-targeted enzyme prodrug cancer therapy utilizing penicillin-V amidase and a doxorubicin prodrug," *J. Drug Target*, 7(1): 43-53 (1999).

Lu, J. Y. and Low, P. S., "Folate targeting of haptens to cancer cell surfaces mediates immunotherapy of syngeneic murine tumors," *Cancer Immunol Immunother*, 51: 153-162 (2002).

Lu, J. Y. and Low, P. S., "Folate-mediated delivery of macromolecular anticancer therapeutic agents," *Adv. Drug Del Rev*, 2002; 54(5): 675-693.

Luo et al., "Efficient syntheses of pyrofolic acid and pteroyl azide, reagents for the production of carboxyl-differentiated derivatives of folic acid," *J. Am. Chem. Soc*., 119: 10004-10013 (1997).

Mack D.O. et al., "The Carboxylation Activity of Vitamin K Analogs with Substitutions at Position 2, 3, or 5," *Journal of Biological Chemistry*, 1979; vol. 254, pp. 2656-2664.

Mancuso A.J. et al., "Activated Dimethyl Sulfoxide: Useful Reagents for Synthesis," *Synthesis*, 1981, pp. 165-184.

March, Advanced Organic Chemistry, 1992, John Wiley & Sons, 4th Ed., pp. 362-363, 816, 885, 896.

Mathais et al., "Receptor-mediated targeting of 67Ga-deferoxamine-folate to folate-receptor-positive human KB tumor xenografts," *Nucl Med Biol*, 26(1): 23-25 (1999).

Mathais et al., "Synthesis of [(99m)Tc]DTPA-folate and its evaluation as a folate-receptor-targeted radiopharmaceutical," *Bioconjug Chem*, 11(2): 253-257 (2000).

Mathias et al., "Indium- 111-DTPA-Folate as a potential folate-receptor-targeted radiopharmaceutical," *J. Nucl. Med*., 39(9): 1579-1585 (1998).

Mathias et al., "Tumor-Selective Radiopharmaceutical Targeting Via Receptor-Mediated Endocytosis of Gallium-67-Deferoxamine-Folate," *J. Nucl. Med*, 37(6): 1003-1008 (1996).

Mathias, C. J., "A kit formulation for preparation of [(111)In]In-DTPA-folate, a folate-receptor-targeted radiopharmaceutical," *Nucl. Med. Biol.*, 25(6): 585-587 (1998).

Matsui et al., "Studies on mitomycins. III. The synthesis and properties of mitomycin derivatives," *J Antibiot*, 21: 189-198 (1968).

Kamao M. et al., "Determination of Plasma Vitamin K by High Performance Liquid Chromatography with Fluorescence Detection Using Vitamin K Analogs as Internal Standards," *Journal of Chromatography B*, 2005; vol. 816, pp. 41-48.

McAlinden TP et al., "Synthesis and Biological Evaluation of a Fluorescent Analogue of Folic Acid," *Biochemistry*, 1991; 30: 5674-81.

McHugh M et al., "Demonstration of a High Affinity Folate Binder in Human Cell Membranes and Its Characterization in Cultured Human KB Cells," *J Biol Chem*, 1979; 254(22):11312-8.

Melani et al., "Targeting of interleukin 2 to human ovarian carcinoma by fusion with a single-chain Fv of antifolate receptor antibody," *Cancer Res*. 58(18): 4146-4154 (1998).

Melby, E.L. et al, "Entry of Protein Toxins in Polarized Epithelial Cells"; *Cancer Research*, 1993; 53: 1755-1760.

Mislick et al., "Transfection of folate-polylysine DNA complexes: evidence for lysosomal delivery," *Bioconjug. Chem*., 6(5): 512-515 (1995).

Mock D.M. et al., "Urinary Biotin Analogs Increase in Humans During Chronic Supplementation: the Analogs are Biotin Metabolites," *Am J Physiol Endocrinol Metab*, 1997; 272: E83-E85.

Morshed et al., "Folate transport proteins mediate the bidirectional transport of 5-methyltetrahydrofolate in cultured human proximal tubule cells," *J. Nutr*., 127(6): 1137-1147 (1997).

Nair et al., "Folate analogs altered in the C9-N10 bridge region. 14. 11-Oxahomofolic acid, a potential antitumor agent", *Journal of Medical Chemistry*, 23: 59-65 (1980).

Nair et al., "Folate analogs altered in the C9-N10 bridge region. 18. Synthesis and antitumor evaluation of 11-oxahomoaminopterin and related compounds," *Journal of Medical Chemistry*, 24: 1068-1073 (1981).

Nair et al., "Folate analogs altered in the C9-N10 bridge region: N10-tosylisohomofolic acid and N10-tosylisohomoaminopterin," *Journal of Medical Chemistry*, 21: 673-677 (1978).

Nair et al., "Folate analogs altered in the C9-N10 bridge region: 11-thiohomofolic acid," *Journal of Medical Chemistry*, 22: 850-855 (1979).

Nair et al., "Folate analogs. 20. Synthesis and antifolate activity of 1',2',3',4',5',6'-hexahydrohomofolic acid," *Journal of Medical Chemistry*, 26: 135-140 (1983).

Nair et al., "Folate analogs. 21. Synthesis and antifolate and antitumor activities of N10-(cyanomethyl)-5,8-dideazafolic acid," *Journal of Medical Chemistry*, 26: 605-607 (1983).

Nair et al., "Folate analogs. 22. Synthesis and biological evaluation of two analogs of dihydrofolic acid possessing a 7,8-dihydro-8-oxapterin ring system," *Journal of Medical Chemistry*, 26: 1164-1168 (1983).

Nair et al., "Folate analogues altered in the C9-N10 bridge region. 10-Oxafolic acid and 10-oxaaminopterin," *Journal of Medical Chemistry*, 19: 825-829 (1976).

Neuss, N. et al., "Vinca Alkaloids. XXX (1). Chemistry Of The Deoxyvinblastines (Deoxy-VLB), Leurosine (VLR), And Pleurosine, Dimeric Alkaloids From Vinca," *Tetrahedron Letters*, No. 7, pp. 783-787 (1968).

Neuzil J. et al., "Vitamin E Analogs: A New Class of Multiple Action Agents with Anti-Neoplastic and Anti-Atherogenic Activity," *Apoptosis*, 2002; vol. 7, pp. 179-187.

Nielsen P. et al., "Phosphates of Riboflavin and Riboflavin Analogs: A Reinvestigation by High-Performance Liquid Chromatography," *Analytical Biochemistry*, vol. 130, 1983, pp. 359-368.

Nishikawa, Yuji et al., "Growth Inhibition of Hepatoma Cells Induced by Vitamin K and Its Analogs," *Journal of Biological Chemistry*, 1995; vol. 270, No. 47, pp. 28304-28310.

Nosaka K.et al., "Separate Determination of Anticoccidial Thiamine Analogs by High-performance Liquid Chromatography," *Acta A Vitaminol. Et Enzymol*, 1984, vol. 6 (2), pp. 137-142.

Oatis et al., "Synthesis of quinazoline analogues of folic acid modified at position 10," *Journal of Medical Chemistry*, 20: 1393-1396 (1977).

Olsnes S. et al., "Immunotoxins-entry into cells and mechanisms of action," *Immunology Today*, 1989; vol. 10, No. 9, pp. 291-295.

Patrick et al., "Folate Receptors As Potential Therapeutic Targets in Choroid Plexus Tumors of Sv40 Transgenic Mice," *J. Neurooncol*,. 32(2): 111-123 (1997).

Patrick et al., "Intracerebral bispecific ligand-antibody conjugate increases survival of animals bearing endogenously arising brain tumors," *Int. J. Cancer*, 78(4): 470-79 (1998).

Peltier, Hillary M., et al., "The Total Synthesis of Tubulysin D," 2006, *J. Am. Chem. Soc*., No. 128, pp. 16018-16019.

Plante et al., "Polyglutamyl and polylysyl derivatives of the lysine analogues of folic acid and homofolic acid," *Journal of Medical Chemistry*, 19: 1295-1299 (1976).

Politis I. et al., "The Effect of Various Vitamin E Derivatives on the Urokinase-Plasminogen Activator System of Ovine Macrophages and Neutrophils," *British Journal of Nutrition*, vol. 89, 2003, pp. 259-265.

Prasad et al., "Functional coupling between a bafilomycin A1-sensitive proton pump and a probenecid-sensitive folate transporter in human placental choriocarcinoma cells," *Biochim. Biophys. Acta*, 1994; 1222(2): 309.

Punj, V. et al., "Effect of Vitamin D Analog (1α Hydroxy D5) Immunoconjugated to Her-2 Antibody on Breast Cancer," *Int. J. Cancer*, 2004; 108: 922-929.

Raghavan B et al., "Cytotoxic Simplified Tubulysin Analogues," *J. Med. Chem*., 2008; 51(6), pp. 1530-1533.

Ranasinghe, M. G. et al.; "A Facile Synthesis of Unsymmetrical Thiolsulfonates via Sulfonylation of Mercaptans," *Synthetic Communications*, 1988; 18(3), pp. 227-232.

Reddy et al., "Optimization of folate-conjugated liposomal vectors for folate receptor-mediated gene therapy," *J. Pharm. Sci*, 88(11): 1112-1118 (1999).

Reddy et al., "Preclinical evaluation of EC145, a folate-vinca alkaloid conjugate," *Cancer Res*., 2007; 67:4434-42.

Reddy et al., "Retargeting of viral vectors to the folate receptor endocytic pathway," *J Control Release*, 74(1-3): 77-82 (2001).

Reddy, J. A., Low, P. S., "Folate-Mediated Targeting of Therapeutic and Imaging Agents to Cancers," *Crit. Rev. Ther. Drug Carrier Syst*., vol. 15, No. 6, 1998, pp. 587-627.

Remington: The Science & Practice of Pharmacy, 21th Edition (Lippincott Williams & Wilkins, 2005).

Renz P. et al., "Synthesis of 4-Aza-5, 6-diethylbenzimidazole and Biosynthetic Preparation of 4- and 7-Aza-5, 6-dimethylbenzimidazolylcobamide," *Z. Naturforsch*, 1997, vol. 52c, pp. 287-291.

Rijnboutt et al., "Endocytosis of GPI-linked membrane folate receptor-alpha," *J. Cell Biol*., 132(1-2): 35-47 (1996).

Roberts et al., "Folic acid analogs. Modifications in the benzene-ring region. 3. Neohomofolic and neobishomofolic acids. An improved synthesis of folic acid and its analogs," *Journal of Medical Chemistry*, 16: 697-699 (1973).

Roberts et al., "Folic acid analogs. Modifications in the benzene-ring region. 2. Thiazole analogs," *Journal of Medical Chemistry*, 15: 1310-1312 (1972).

Roberts et al., "Folic acid analogs. Modifications in the benzene-ring region. 1. 2'- and 3'-Azafolic acids," *Journal of Medical Chemistry*, 14: 125-130 (1971).

Roberts et al., "Folic acid analogs. Modifications in the benzene-ring region. 4. 3'-Ethyl- and 3'-isopropylfolic acids," *Journal of Medical Chemistry*, 17: 219-222 (1974).

Rose W.C., "Taxol-Based Combination Chemotherapy And Other In Vivo Preclinical Antitumor Studies," *J Natl Cancer Inst Monogr*, 1993, No. 15, pp. 47-53.

Ross et al., "Differential regulation of folate receptor isoforms in normal and malignant tissues in vivo and in established cell lines. Physiologic and clinical implications," *Cancer*, 73(9): 2432-2443, (1994).

Rothberg et al, "Cholesterol controls the clustering of the glycophospholipid-anchored membrane receptor for 5-methyltetrahydrofolate," *J. Cell Biol*., 111(6): 2931-2938 (1990).

Rothberg et al., "The glycophospholipid-linked folate receptor internalizes folate without entering the clathrin-coated pit endocytic pathway," *J. Cell Biol*., 110(3): 637-649 (1990).

Roy et al., "Targeting T cells against brain tumors with a bispecific ligand-antibody conjugate," *Int. J. Cancer* 76(5): 761-66 (1998).

Sadasivan et al., "The complete amino acid sequence of a human folate binding protein from KB cells determined from the cDNA," *J. Biol. Chem.*, 1989; 264: 5806-5811.

Sargent D.R. et al., "Antimetabolites of Pantothenic Acid, Ureido— and Carbamoyl-Derivatives," *Texas Reports on Biology and Medicine*, 1975, vol. 33, No. 3, pp. 433-443.

Sasse F. et al., "Tubulysins, New Cytostatic Peptides from Myxobacteria Acting on Microtubuli Production, Isolation, Physico-Chemical and Biological Properties," *The Journal of Antibiotics*, 2000; vol. 53, No. 9, pp. 879-885.

Search Report for Taiwan Patent Application No. 093101735, dated Jul. 14, 2007, 1 page.

Senter et al., "Development of a Drug-Release Strategy Based on the Reductive Fragmentation of Benzyl Carbamate Disulfides," *J. Org. Chem.*, 55: 2975-2978 (1990).

Shimizu M. et al., "Synthesis and biological activities of new 1alpha, 25-dihydroxy-19-norvitamin D3 analogs with modifications in both the A-ring and the side chain," *Bioorganic & Medicinal Chemistry*, 2006; 14(12): 4277-94.

Shimizu, Kazui, et al., "Novel vitamin D3 antipsoriatic antedrugs: 16-En-22-oxa-1a,25-(OH)2D3 analogs," *Bioorganic & Medicinal Chemistry*, 2006;14: 1838-1850.

Shoup T.M. et al., "Synthesis of Fluorine-18-Labeled Biotin Derivatives: Biodistribution and Infection Localization," *J. Nucl. Med.*, 1994; 35: 1685-1690.

Skinner W.A. et al., "Structure-Activity Relations in the Vitamin E Series. II. Derivatives of α-Tocopherol Substituted at the 5-Methyl Group," *J. Med. Chem.*, 1969; 12 (1): 64-66.

Smart et al., "Clustered folate receptors deliver 5-methyltetrahydrofolate to cytoplasm of MA104 cells," *J. Cell Biol.*, 134(5): 1169-1177 (1996).

Smart et al., "Protein kinase C activators inhibit receptor-mediated potocytosis by preventing internalization of caveolae," *J. Cell Biol.*, 124(3): 307-313 (1994).

Spry C. et al., "A Class of Pantothenic Acid Analogs Inhibits Plasmodium Falciparum Pantothenate Kinase and Represses the Proliferation of Malaria Parasites," *Antimicrobial Agents and Chemotherapy*, 2005; 49(11): 4649-4657.

Steinberg, G. et al., "Synthesis and Evaluation of Pteroic Acid-Conjugated Nitroheterocyclic Phosphoramidates as Folate Receptor-Targeted Alkylating Agents," *J. Med. Chem.* 44: 69-73 (2001).

Steinmetz, H. et al., "Isolation, Crystal and Solution Structure Determination, and Biosynthesis of Tubulysins-Powerful Inhibitors of Tubulin Polymerization from Microbacteria", *Angew. Chem. Int. Ed.*, 2004, No. 43, pp. 4888-4892.

Takahata Y. et al., "Synthesis, Properties and Microbiological Activity of Hydrophobic Derivatives of Vitamin B12," *J. Nutr. Sci. Vitaminol.*, 1995, vol. 41, pp. 515-526.

Takasu, H. et al., "c-Fos protein as a target of anti-osteoclastogenic action of vitamin D, and synthesis of new analogs," *The Journal of Clinical Investigation*, 2006; vol. 116, No. 2, pp. 528-535.

Takeda, K. et al., "A Synthesis of a New Type of Alkoxycarbonylating Reagents from 1,1-Bis[6-(trifluoromethyl)benzotriazolyl] Carbonate (BTBC) and Their Reactions," *Sythesis*, 1987; 6: 557-560.

Temple et al., "Synthesis of pseudo cofactor analogs as potential inhibitors of the folate enzymes," *Journal of Medical Chemistry*, 25: 161-166 (1982).

Theti, D. S. et al., "Selective delivery of CB300638, a cyclopenta[g]quinazoline-based thymidylate synthase inhibitor into human tumor cell lines overexpressing the alpha-isoform of the folate receptor," Cancer Res, 2003; 63(13): 3612-3618.

Toffoli et al., "Overexpression of folate binding protein in ovarian cancers," *Int. J. Cancer* 74(2): 193-198 (1997).

Toraya T. et al., "Immobilized Derivatives of Vitamin B12 Coenzyme and Its Analogs," *Methods in Enzymology*, vol. 67, pp. 57-66, 1980.

Toraya T. et al., "The Synthesis of Several Immobilized Derivatives of Vitamin B12 Coenzyme and Their Use as Affinity Adsorbents for a Study of Interactions of Diol Dehydrase with the Coenzyme," *The Journal of Biological Chemistry*, 1990; vol. 255, No. 8, pp. 3520-3525.

Trachewsky D., "Antihypertensive Effect of Riboflavin Analogs in Rats with Mineralocorticoid-Induced Hypertension," *Hypertension*, 1981; vol. 3, No. 1, pp. 75-80.

Truneh A. et al., "Temperature-sensitive differential affinity of TRAIL for its receptors. DR5 is the highest affinity receptor," *J Biol Chem*, 2000; 275(30):23319-25.

Turek et al., "Endocytosis of folate-protein conjugates: ultrastructural localization in KB cells," *J. Cell Sci.* 106: 423-430 (1993).

Turk et al., "Characterization of a novel pH-sensitive peptide that enhances drug release from folate-targeted liposomes at endosomal pHs," *Biochim Biophys Acta*, 1559(1): 56-68 (2002).

Ueda M. et al., "Effect of Vitamin B12 Derivatives on Urinary Excretion of Methylmalonic Acid in Liver Diseases," *Acta Med. Okayama*, 1970; vol. 24, pp. 365-372.

Varma, R. et al., "GPI-anchored proteins are organized in submicron domains at the surface," *Nature*, 394(6695): 798-801 (1998).

Verwey, J., "Mitomycin C-Induced Renal Toxicity, a Dose-Dependent Side Effect?," *Eur J Cancer Clin Onco*, 1987; vol. 23, No. 2, pp. 195-199.

Vesely D.L. et al., "Biotin Analogs Activate Guanylate Cyclase," *Molecular and Cellular Biochemistry*, 1984; vol. 60, pp. 109-114.

Vlahov I.R. et al., "Design and regioselective synthesis of a new generation of targeted chemotherapeutics. Part 1: EC145, a folic acid conjugate of desacetylvinblastine monohydrazide," *Bioorg Med Chem Lett*, 2006; 16(19):5093-6.

Vogel et al., "Peptide-Mediated Release of Folate-Targeted Liposome Contents From Endosomal Compartments," *J. Am. Chem. Soc.*, 1996; 118(7): 1581-1586.

Vyas D. et al., "A practical synthesis of mitomycin A and its analogs," *J Org Chem*, 1986; 31:4307-4309.

Wang et al., "Delivery of antisense oligodeoxyribonucleotides against the human epidermal growth factor receptor into cultured KB cells with liposomes conjugated to folate via polyethylene glycol," *Proc. Natl. Acad. Sci. USA*, 92(8): 3318-3322 (1995).

Wang et al., "Design and synthesis of [111In]DTPA-folate for use as a tumor-targeted radiopharmaceutical," *Bioconjug Chem.*, 8(5): 673-679 (1997).

Wang et al., "Synthesis, purification, and tumor cell uptake of 67Ga-deferoxamine—folate, a potential radiopharmaceutical for tumor imaging," *Bioconj. Chem.*, 1996; 7(1): 56-62.

Wang S. et al., "Folate-mediated targeting of antineoplastic drugs, imaging agents, and nucleic acids to cancer cells," *J. Control Rel*, 1998; 53(1-3): 39-48.

Wang, Xiu-Fang et al., "Vitamin E Analogs Trigger Apoptosis in HER2/erbB2-Overexpressing Breast Cancer Cells by Signaling Via the Mitochondrial Pathway," *Biochemical and Biophysical Research Communication*, 2005; vol. 326, pp. 282-289.

Weinstock et al., "Folic acid analogs. II. p-{[(2,6-Diamino-8-purinyl)methyl]amino}-benzoyl-L-glutamic acid and related compounds," *Journal of Medical Chemistry*, 13: 995-997 (1970).

Weitman et al., "Cellular localization of the folate receptor: potential role in drug toxicity and folate homeostasis," *Cancer Res.*, 1992; 52(23): 6708-6711.

Weitman et al., "Distribution of the folate receptor GP38 in normal and malignant cell lines and tissues," *Cancer Res.*, 1992; 52(12): 3396-3401.

Westerhof G.R. et al., "Carrier- and Receptor-Mediated Transport of Folate Antagonists Targeting Folate-Dependent Enzymes: Correlates of Molecular-Structure and Biological Activity," *Molecular Pharmacology*, 1995, 48, pp. 459-471.

Westerhof GR et al., "A photoaffinity analogue of folic acid as a probe for the identification and function of a membrane folate binding protein (mFBP) in human CCRF-CEM leukemia cells," *Proceedings of the American Association for Cancer Research*, 1991; 32:328.

Wiener et al., "Targeting dendrimer-chelates to tumors and tumor cells expressing the high-affinity folate receptor," *Invest. Radiol.* 32(12): 748-54 (1997).

Wu M. et al., "Clustering of GPI-anchored folate receptor independent of both cross-linking and association with caveolin," *J. Membr. Biol.* 159(2): 137-147 (1997).

Zimmerman, J., "Folic acid transport in organ-cultured mucosa of human intestine. Evidence for distinct carriers," *Gastroenterol.* 99(4): 964-972 (1990).

International Search Report for PCT/US2006/009153, dated Oct. 31, 2006.

Leamon Christopher P., "Aspects of Folate-Mediated Drug Delivery . . . Beyond Purdue" PowerPoint Presentation presented at Purdue University on May 4, 1999, (22 pages).
Achilefu et al. "A New Method for the Synthesis of Tri-tert-butyl Diethylenetriaminepentaacetic Acid Its Derivatives" *J. Org. Chem.* 2000;65:1562-1565.
Carl et al. "A novel connector linkage applicable in prodrug design" J. Med. Chem. 1981;24(5):479-480.
Coney et al. "Cloning of a tumor-associated antigen: MOv18 and MOv19 antibodies recognize a folate-binding protein" Cancer Res. 1991;51(22):6125-32.
Crapatureanu et al. "Molecular necklaces. Cross-linking hemoglobin with reagents containing covalently attached ligands" Bioconjugate Chemistry, 1999;10(6):1058-67.
Darnell, Ed. Molecular Cell Biology W. H. Freeman, San Francisco 1990;326-333.
DeNardo, Gerald. "When is Too Much Too Much and Yet Not Enough? Alas, a Plethora of Opportunities but Where's the Beef?" J. of Nuclear Medicine 2000; 41(3):470-3.
Dorwald, F. Z., "Side Reactions in Organic Synthesis: A Guide To Successful Synthesis Design," Wiley-VCII, Weinheim, 2005, p. ix of preface.
Forgac. "Structure and function of vacuolar class of ATP-driven pumps" Physiological Rev. 1989; 69(3):765-795.
Garrett et al. "Synthesis and characterisation of polyamine-poly(ethylene glycol) constructs for DNA binding and gene delivery" Bioorganic & Medicinal Chemistry, 2000; 8(7):1779-1797.
Henderson et al. "Mediated uptake of folate by a high-affinity binding protein in sublines of L1210 cells adapted to nanomolar concentrations of folate" J. Membrane Biol., 1988;101:247-258.
Huang et al. "Design, syntheses and sequence selective DNA cleavage of functional models of bleomycin-II. 1,2 -trans-di substituted cyclopropane units as novel linkers" Bioorganic & Medicinal Chemistry, 1995;3(6):647-57.
Jansen et al., "Identification of a Membrane-Associated Folate-Binding Protein in Human Leukemic CCRF-CEM Cells with Transport-Related Methotrexate Resistance"in Cancer Res., 1989, 49, 2455-2459.
Jansen, "Receptor- and Carrier-Mediated Transport Systems for Folates and Antifolates," Antifolate Drugs in Cancer Therapy, Jackman, Ed., Humana Press Inc, Totowa NJ (1999): 293-321.
Jansen et al. "The Reduced Folate/Methotrexate Carrier and a Membrane-Associated Folate Binding Protein as Transport Routes for Novel Antifolates: Structure-Activity Relationship" Chemistry and Biology of Pteridines and Folates New York, 1992;767-770.
Kamen et al., 1986, "Receptor-mediated folate accumulation is regulated by cellular folate content" Proc. Natl. Acad. Sci., U.S.A. 83, 5983-5987.
Ke et al. "Targeting the Tumor-Associated Folate Receptor with a 111- IN-DTPA Conjugate of Pteroic Acid" Abstract No. 427. 48th Annual Meeting of the Society of Nuclear Medicine Toronto, Canada, Jun. 26, 2001, available May 4, 2001; 1 pg.
Kemp et al. "New Protective Groups for Peptide Synthesis-I The Bic Group Base and Solvent Lability of the 5 -B enzi soxazolymethyl eneoxycarbonyl amino function" Tet. Lett. 1975;52:4625-4628.
Kutsky RJ. Handbook of Vitamins, Minerals, and Hormones, 2nd Edition. New York: Van Nostrand Reinhold: 1981;263-277.
Lee et al. "Prolonged circulating lives of single-chain Fv proteins conjugated with polyethylene glycol: a comparison of conjugation chemistries and compounds" Bioconjugate Chemistry, 1999;10(6):973-81.
Li et al. "Local concentration of folate binding protein GP38 in sections of human ovarian carcinoma by concentration of in vitro quantitative autoradiography." J. Nucl. Med. 1996; 37:665-672.
Linder et al., In vitro & in vivo studies with a-and y-isomers of 99'Tc-oxa folate show uptake of both isomers in folate receptor (+) KB Cell Lines J. Nuclear Med. 2000;41(5):470 Suppl.
Mehvar R "Dextrans for targeted and sustained delivery of therapeutic and imaging agents" [Review] Journal of Controlled Release, 2000;69(1):1-25.

Mezzanzanica et al. "Human T-lymphocytes targeted against an established human ovarian carcinoma with a bispecific F(ab')2 antibody prolong host survival in a murine xenograft model" Cancer Res. 1991; 51:5716-5721.
Miotti et al., "Characterization of Human Ovarian Carcinoma-Associated Antigens Defined by Novel Monoclonal Antibodies with Tumor-Restricted Specificity" Int. J. Cancer, 1987;39:297-303.
Pastan et al, eds. "The Pathways of Endocytosis" Endocytosis, Plenum Press, New York 1985;1-40.
Peterson et al. "Enzymatic cleavage of peptide-linked radiolabels from immunoconjugates" Bioconjugate Chemistry, 1999;10(4):553-7.
Pizzorno et al. "5,10-Dideazatetrahydrofolic acid (DDATHF) transport in CCRFCEM and MA104 cell lines." J. Biol, Chem., 1993; 268(2):247-258.
Rothenberg et al. "Further observations on the folate-binding factor in some leukemic cells" J. Clin. Invest. 1971; 50(3):719-726.
Selhub et al. "The folate binding protein of rat kidney. Purification, properties, and cellular distribution" J. Biol. Chem. 1984;259(10):6601-6606.
Selhub et al. "Renal folate adsorption and the kidney folate binding protein I. Urinary Clearance studies" Am. J Physiol. 252:F750-F756.
Selhub et al. "Renal folate adsorption and the kidney folate binding protein II. Microinfusion studies" Am. J. Physiol. 252:F757-F760, 1987.
Sirotnak. "Obligate genetic expression in tumor cells of a fetal membrane property mediating "Folate" transport: biological significance and implications for improved therapy of human cancer" Cancer Res., 1985;45(9):3992-4000.
Stein et al. "Normal tissue reactivity of four anti-tumor monoclonal antibodies of clinical interest" Int. J. Cancer 1991;47(2):163-169.
Tanaka et al. "Preparation and characterization of a disulfide-linked bioconjugate of annexin V with the B-chain of urokinase: an improved fibrinolytic agent targeted to phospholipid-containing thrombi" Biochemistry, 1996;35(3):922-9.
Thaden et al. "Photoaffinity behavior of a conjugate of oligonucleoside methylphosphonate, rhodamine, and psoralen in the presence of complementary oligonucleotides" Bioconjugate Chemistry, 1993;4(5):386-94.
Toffoli et al. "Expression of folate binding protein as a prognostic factor for response to platinum-containing chemotherapy and survival in human ovarian cancer" Int. J. Cancer (Pred. Oncol) 1998; 79:121-126.
Westerhof et al. "Membrane transport of natural folates and antifolate compounds in murine L1210 Leukemia cells: role of carrier-and receptor mediated transport systems" Cancer Res. 1991;51:5507-5513.
Williams et al. "Renal tubular transport of folic acid and methotrexate in the monkey" Am. J. Physiol 1982; 242(5):F484-490.
Weygand, et al., Chemishe. Berichte (1950) 83, 460-467.
Beevers, Christopher S., et al., "Curcumin Inhibits the Mammalian Target of Rapamycin-Mediated Signaling Pathways in Cancer Cells", 2006; *Int. Journal Cancer*; Vo. 119; pp. 757-764.
Brown, Nicole E., et al., "Delayed Cystogenesis and Increased Ciliogenesis Associated with th Re-Expression of Polaris in Tg737 Mutant Mice", 2003, *Kidney International*, vol. 63, pp. 1220-1229.
Bukanov Nikolay, O. et al., "Long-Lasting Arrest Of Murine Polycystic Kidney Disease With CDK Inhibitor Roscovitine", Dec. 14, 2006; *Nature*; vol. 444; pp. 949-952.
Hay, Nissim, et al., "Upstream and Downstream of mTOR", 2004, *Genes & Development*, vol. 18, No. 16, pp. 1926-1945.
Kennedy, Michael D., et al., "Evaluation of Folate Conjugate Uptake and Transport by the Choroid Plexus of Mice", (May 2003), vol. 20, No. 5, pp. 714-719.
Leamon, Christopher P., et al., "Folate-Liposome-Mediated Antisense Oligodeoxynucleotide Targeting to Cancer Cells: Evaluation in Vitro and in Vivo", 2003, *Bioconjugate Chemistry*, vol. 14, No. 4, pp. 738-747.
Nauta, Jeroen, et al., "Renal and Biliary Abnormalities in a New Murine Model of Autosomal Recessive Polycystic Kidney Disease", 1993, *Pediatr. Nephrol*. No. 7, pp. 163-172.

Piontek, Klaus B., et al. "A Functional Floxed Allele of *Pkd1* that Can Be Conditionally Inactivated In Vivo", *J. Am. Soc. Nephrol.* vol. 15, pp. 3035-3043, 2004.

Shillingford, Jonathan M., et al., "The mTOR Pathway is Regulated by Polycystin-1, and its Inhibition Reverses Renal Cystogenesis in Polycyctic Kidney Disease", Apr. 4, 2006, *PNAS.* vol. 103, No. 14, pp. 5466-5471.

Ke Cy et al., "Folate-Receptor-Targeting of In-111 Using Pteroic Acid Conjugates of Benzyl-DTPA and Benzyl-DOTA," J. Nucl. Med., 2004; 45(5):457P.

Regueiro-Ren et al., "Synthesis and Biological Activity of Novel Epothilone Aziridines," Organic Letters, 2001; vol. 3, No. 17: 2693-96.

Kamen et al., "A review of folate receptor alpha cycling and 5-methyltetrahydrofolate accumulation with an emphasis on cell models in vitro," Advanced Drug Delivery Reviews, 2004; vol. 56:1085-97.

Elnakat et al., "Distribution, functionality and gene regulation of folate receptor isoforms: implications in targeted therapy," Advanced Drug Delivery Reviews, 2004; vol. 56:1067-84.

Sabharanjak et al., "Folate receptor endocytosis and trafficking," Advanced Drug Delivery Reviews, 2004; vol. 56: 1099-1109.

Paulos et al., "Folate receptor-mediated targeting of therapeutic and imaging agents to activated macrophages in rheumatoid arthritis," Advanced Drug Delivery Reviews, 2004; vol. 56: 1205-17.

Antony, "Folate receptors: reflections on a personal odysssey and a perspective on unfolding truth," Advanced Drug Delivery Reviews, 2004; vol. 56: 1059-66.

Lu et al., "Folate receptor-targeted immunotherapy of cancer: mechanism and therapeutic potential," Advanced Drug Delivery Reviews, 2004; vol. 56: 1161-76.

Roy et al., "Folate-mediated targeting of T cells to tumors," Advanced Drug Delivery Reviews, 2004; vol. 56: 1219-31.

Ke et al., "Folate-receptor-targeted radionuclide imaging agents," Advanced Drug Delivery Reviews, 2004; vol. 56: 1143-60.

Gabizon et al., "Tumor cell targeting of liposome-entrapped drugs with phospholipid-anchored folic acid-PEG Conjugates," Advanced Drug Delivery Reviews, 2004; vol. 56: 1177-92.

Zhao et al., "Tumor-selective targeted delivery of genes and antisense oligodeoxyribonucleotides via the folate receptor," Advanced Drug Delivery Reviews, 2004; vol. 56: 1193-1204.

Paulos CM et al., "Ligand Binding and Kinetics of Folate Receptor Recycling in Vivo: Impact on Receptor-Mediated Drug Delivery," Molecular Pharmacology, 2004; 66:1406-1414.

Griesser UJ, "The Importance of Solvents," in Polymorphism in the Pharmaceutical Industry, Hilfiker ed., 2006; p. 211-230.

Wikipedia, Structural analog, http://en.wikipedia.org/wiki/Structural_analog, downloaded Apr. 7, 2009.

Wikipedia, Functional analog, http://en.wikipedia.org/wiki/Functional_analog, downloaded Apr. 7, 2009.

Wikipedia, Folic acid, http://en.wikipedia.org/wiki/Folic_acid, downloaded Apr. 7, 2009.

Lee JW et al., "Reduction of azides to primary amines in substrates bearing labile ester functionality. Synthesis of a PEG-solubilized, "Y"-shaped iminodiacetic acid reagent for preparation of folate-tethered drugs," Organic Letters, 1999; 1(2):179-181.

J. Semb, J. H. Boothe, R. B. Angier, C. W. Waller, J. H. Mowat, B. L. Hutchings, Y. SubbaRow, "Pteroic Acid Derivatives. V. Pteroyl-α-glutamyl-α-glutamylglutamic Acid, Pteroyl-γ-glutamyl-α-glutamylglutamic Acid, Pteroyl-α-glutamyl-γ-glutamylglutamic Acid," JACS, 1949, 71 (7), pp. 2310-2315.

D. B. Cosulich, J. M. Smith Jr., "Analogs of Pteroylglutamic Acid. I. N10-Alkylpteroic Acid and Derivatives," JACS, 1948, 70 (5), pp. 1922-1926.

E. M. Birinberg, G. D. Glebova, N. A. Andreeva and V. M. Berezovskii, "Synthesis and antimetabolic activity of pyrimidine analogs of folic and pteroic acids," Pharmaceutical Chemistry Journal, 1969, 3 (6), pp. 331-333.

H. Zimmer, R. Atchley, "Potential anticancer agents V., Synthesis of folic acid and pteroic acid analogs derived of caffeine and theophylline," Arzneimittelforschung, 1966, 16(4), pp. 541-545.

G. Pizzorno, J. A. Sokoloski, A. R. Cashmore, B. A. Moroson, A. D. Cross, G.P. Beardsley, "Intracellular metabolism of 5,10-dideazatetrahydrofolic acid in human leukemia cell lines," Molecular Pharmacology, 1991, 39 (1), pp. 85-89.

R. I. Ho, L. Corman, J. Ho, M. G. Nair, "A simple radioassay for dihydrofolate synthetase activity in *Escherichia coli* and its application to an inhibition study of new pteroate analogs," Anal. Biochem. 1976, 73(2), pp. 493-500.

R. H. Nimmo-Smirth, D.J. Brown, "Some Effects of 2-deaminopteroylglutamic Acid upon Bacterial Growth," J. Gen. Microbial. 1953, 9, pp. 536-544.

Y. H. Kim, Y. Gaumont, R. L. Kisliuk, H.G. Mautner, "Synthesis and biological activity of 10-thia-10-deaza analogs of folic acid, pteroic acid, and related compounds," J Med Chem. 1975, 18 (8), pp. 776-780.

GE Healthcare, Instructions 71-7104-00 AD, 2007.

Atkinson SF et al., "Conjugation of folate via gelonin carbohydrate residues retains ribosomal-inactivating properties of the toxin and permits targeting to folate receptor positive cells," Journal of Biological Chemistry, 2001; 276(30):27930-27935.

Matulic-Adamic J et al., "An efficient synthesis of the ribozyme-folate conjugate," Tetrahedron Letters, 2002; 43(25):4439-4441.

Harrison JG et al., A convenient synthetic route to oligonucleotide conjugates,: Bioorganic & Medicinal Chemistry Letters, 1997; 7(8): 1041-1046.

Dyson G., May P. "The Chemistry of Synthetic Pharmaceutical Substances", translation from English M.:—"The World", 1964, pp. 12-19.

Mashkovskiy M.D. Drugs, Moscow, New wave, 2001, vol. I, p. 11.

Pathalk et al., Enzymic protecting group techniques in organic synthesis, Stereosel. Biocatal. 775-797 (2000).

Conrad et al, "Structure-Activity Relationships of Dimeric Catharanthus Alkaloids. 2. Experimental Antitumor Activates of N-Substituted Deacetylvinblastine Amide (Vindesine) Sulfates," Journal of Medicinal Chemistry, 1979, 22(4): 391-400.

Dube et al., "Preparation and Tumor Cell Uptake of Poly(N-isopropylacrylamide) Folate Conjugates," Bioconjugate Chem, 2002; 13: 685-692.

Evans et al., "Synthesis of biotin conjugates of the antifungal compound cymoxanil," Pest Manag Sci, 2002; 58:392-396.

Rao et al., "Vinblastin-23-oyl Amino Acid Derivatives: Chemistry, Physicochemical Data, Toxicity, and Antitumor Activities Against P388 and L1210 Leukemias," Journal of Medicinal Chemistry, 1985, 28:1079-1088.

GE Healthcare, Instructions 71-7104-00 AD. 2003.

\* cited by examiner

_US 8,044,200 B2_

SYNTHESIS AND PURIFICATION OF PTEROIC ACID AND CONJUGATES THEREOF

CROSS-REFERENCE TO RELATED APPLICATIONS

This application is a U.S. national application under 37 C.F.R. §371(b) of International Application Serial No. PCT/US2006/009153 filed Mar. 14, 2006, which claims the benefit under 35 U.S.C. §119(e) of U.S. Provisional Application Ser. No. 60/662,277, filed Mar. 16, 2005, the disclosure of which is hereby incorporated by reference.

TECHNICAL FIELD

This invention pertains to the purification of pteroic acid and derivatives of pteroic acid, and to the purification of pteroic acid, and analogs and derivatives of pteroic acid, conjugated to other compounds. This invention also pertains to methods for preparing pteroic acid, and analogs and derivatives of pteroic acid, conjugated to other compounds. This invention also pertains to methods for treating patients with pteroic acid, and analogs and derivatives of pteroic acid, conjugated to other compounds.

BACKGROUND

Pteroic acid is a convenient starting material for making folate derivatives that can be conjugated to drugs for use as conjugates in therapies that include vitamin receptor-based targeting. Vitamin-drug conjugates can be targeted, for example, to cancer cells that uniquely express, over-express, or preferentially express vitamin receptors. Illustratively, pteroic acid has been used as the starting material for the preparation of a conjugate comprising a folic acid derivative linked to fluorescein via a gamma carboxyl-linked ethylene diamine bridge. This conjugate is described in U.S. patent application Ser. No. 09/822,379, the disclosure of which is incorporated herein by reference. The conjugate is used to label pathogenic cells, such as cancer cells, with fluorescein to make the cancer cells antigenic resulting in their recognition and elimination by the host immune system.

Pteroic acid may be prepared by a variety of conventional means including by synthesis, microbial degradation of folic acid, enzymatic degradation of folic acid, hydrolysis of folic acid, and other conventional methods. Generally, pteroic acid prepared by these methods is contaminated by folio acid, often in substantial amounts. For example, pteroic acid prepared by enzymatic degradation can contain as much as 25% folic acid. Accordingly, efficient methods are needed to remove folic acid contaminants and other impurities from preparations of pteroic acid.

Vitamin-drug conjugates, including conjugates of pteroic acid may be prepared using synthetic methods. In some cases, those synthetic methods may also lead to the formation of side products, impurities, or other contaminants. Accordingly, synthetic and/or purification methods are needed to either avoid the formation of these side products, impurities, or other contaminants, or to remove these side products, impurities, or other contaminants from the vitamin-drug conjugates.

SUMMARY OF THE INVENTION

Methods for purifying pteroic acid, derivatives of pteroic acid, and combinations thereof are described. In one illustrative embodiment for purifying pteroic acid, derivatives of pteroic acid, and combinations thereof by chromatography, methods are described herein that include the steps of (a) contacting a solution comprising pteroic acid, the derivative of pteroic acid, or the combination thereof with an ion exchange chromatographic support; (b) eluting a first fraction comprising pteroic acid, the derivative of pteroic acid, or the combination thereof with a mobile phase having a pH of about 10 or greater; (c) lowering the pH of the first fraction to about 3 or less; and (d) precipitating pteroic acid, the derivative of pteroic acid, or the combination thereof.

In another illustrative embodiment for purifying pteroic acid, derivatives of pteroic acid, and combinations thereof by chromatography, methods are described herein that include the steps of (a) contacting a solution comprising pteroic acid, the derivative of pteroic acid, or the combination thereof, with an anion exchange chromatographic support; and (b) eluting a first fraction comprising pteroic acid, the derivative of pteroic acid, or the combination thereof.

The methods described herein may also optionally include the step of (e) eluting a second fraction comprising folic acid, a derivative of folic acid, or a combination thereof, where the first fraction and the second fraction are substantially separated. Substantial separation includes separation as determined by time, by a predetermined number of fractions, or other quantitative or qualitative assessment indicating that the first and second fraction are not substantially overlapping during the elution of the first and second fractions.

Chromatographic supports for the chromatography methods described herein include but are not limited to ion-exchange resins, anion-exchange resins, saccharide-based resins, saccharide-based ion-exchange resins, saccharide-based anion-exchange resins, and the like. Mobile phases for the chromatography methods described herein include but are not limited to aqueous phases having a pH of about 10 or greater, about 11 or greater, or having a pH in the range from about 11 to about 13. In one illustrative variation, the mobile phase is free of or substantially free of ammonia or salts thereof. Mobile phases for the chromatography methods described herein may also optionally include organic cosolvents, such as acetone, tetrahydrofuran, acetonitrile, alcohols, including MeOH, EtOH, and the like, and others.

In another illustrative embodiment, methods for purifying conjugates comprising pteroic acid or a derivative thereof, and fluorescein or a derivative thereof are described. In one aspect, those methods include the steps of (a) contacting a solution comprising the conjugate with a first reversed phase chromatographic support; (b) eluting a first fraction comprising a phosphate complex of the conjugate with a mobile phase, said mobile phase comprising a phosphate salt and having a pH in the range from about 6 to about 8; (c) contacting the first fraction with a second reversed phase chromatographic support; and (d) eluting a second fraction comprising the conjugate with a mobile phase comprising water, where the second fraction is substantially free of phosphate.

Chromatographic supports for the chromatography methods described herein include but are not limited to reverse-phase resins, such as C8 resins, C18, resins, capped versions thereof, and the like. Mobile phases for the chromatography methods described herein include but are not limited to aqueous phases having a pH near neutrality, or slightly above neutrality, including a pH in the range from about 7.1 to about 7.7, and illustratively a pH of about 7.4. In one illustrative variation, the mobile phase includes one or more phosphate salts. In another illustrative variation, the mobile phase is free of or substantially free of phosphate. Mobile phases for the chromatography methods described herein may also optionally include organic cosolvents, such as MeOH, EtOH, acetone, tetrahydrofuran, acetonitrile, and the like.

In another illustrative embodiment, the methods described herein are performed to give purified compounds and compositions, including pteroic acid, derivatives of pteroic acid, and combinations thereof, and conjugates comprising pteroic acid or a derivative thereof, and fluorescein or a derivative thereof having predetermined purities, including purities of about 95% or greater, 98% or greater, and 99% or greater. As used herein, purity determinations may be based on weight percentage, mole percentage, and the like. In addition, purity determinations may be based on the absence or substantial absence of certain predetermined components, such as folic acid, fluorescein components, bisfluorescein components, and the like. It is also to be understood that purity determinations are applicable to solutions of the compounds and compositions purified by the methods described herein. In those instances, purity measurements, including weight percentage and mole percentage measurements, are related to the components of the solution exclusive of the solvent.

In another illustrative embodiment, processes for preparing conjugates of pteroic acid or derivatives thereof, and fluorescein or derivatives thereof are described.

In another illustrative embodiment, compounds and compositions having certain predetermined purity requirements are described. In one aspect, the compounds and/or compositions include pteroic acid, derivatives of pteroic acid, and combinations thereof. In another aspect, the compounds and/or compositions include conjugates of pteroic acid or derivatives thereof, and fluorescein or derivatives thereof. In one variation, purity requirements of illustrative compounds and/or compositions described herein include including purities of about 95% or greater, 98% or greater, and 99% or greater, and may be based on weight percentage, mole percentage, and the like. In another variation, purity requirements of illustrative compounds and/or compositions described herein include purity determinations based on the absence or substantial absence of certain predetermined components, such as folic acid, fluorescein components, bisfluorescein components, and the like.

In another illustrative embodiment, methods for treating patients, mammals, or animals in need of relief from disease states responsive to the mediation or elimination of pathogenic cells are described. In one aspect, methods for enhancing an endogenous immune response-mediated elimination of a population of pathogenic cells in a patient, mammal, or animal is described. Illustrative methods described herein include the steps of administering to the patient, mammal, or animal in need of relief an effective amount of a composition comprising a ligand-fluorescein conjugate. In another illustrative aspect, methods are described herein where the composition administered to the patient, mammal, or animal in need of relief, includes a predetermined maximum level of one or more bisfluorescein components, such as no more than 0.1% or 0.05%, or is free of or, substantially free of one or more bisfluorescein components.

It is appreciated that the synthetic methods described herein may be used alone or in combination with the purification methods described herein for providing vitamin-drug conjugates.

DETAILED DESCRIPTION

Figure 1A:
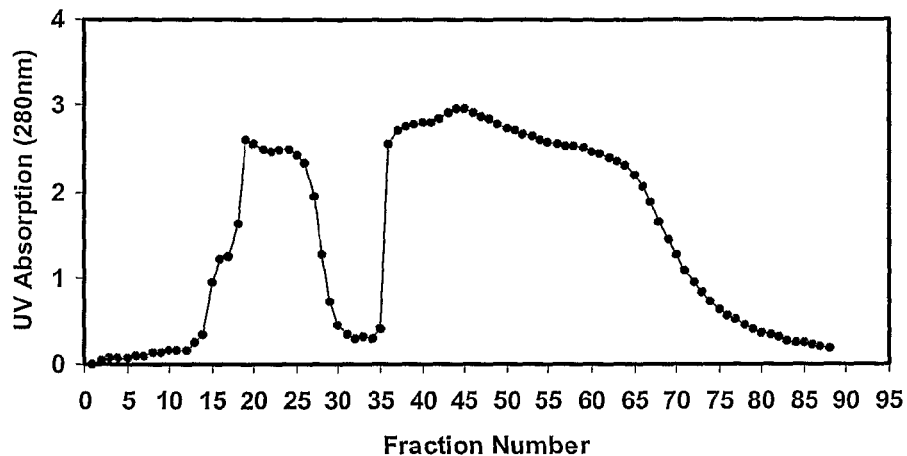
FIG. 1A shows the UV absorption at 280 nm of fractions eluted from a DEAE cellulose column (DE32) in the purification of pteroic acid.

Methods for purifying pteroic acid, derivatives and analogs of pteroic acid, and/or combinations thereof are described herein. In one embodiment, the methods include the steps of (a) contacting a solution comprising pteroic acid, derivatives or analogs of pteroic acid, and/or combinations thereof, with an ion exchange chromatographic support; (b) eluting a first fraction comprising pteroic acid, derivatives or analogs of pteroic acid, and/or combinations thereof, with a mobile phase having a pH of about 10 or greater; and (c) lowering the pH of the first fraction to about 3 or less; and (d) precipitating pteroic acid, derivatives or analogs of pteroic acid, and/or combinations thereof.

In one variation, the methods described herein may also include the step of (e) eluting a second fraction comprising folic acid, derivatives of folic acid, or combinations thereof, where the first fraction and the second fraction are substantially separated. Substantial separation may be determined by any number of objective quantitative or qualitative criteria, including but not limited to elapsed time, fraction number, baseline evaluation, or other method that assesses the degree of overlap between the eluting fractions, and therefore the likelihood and degree of possible cross-contamination of the first and/or second fractions. It has been observed that for certain saccharide-based chromatographic supports or resins, the folic acid fraction elutes prior in time to the pteroic acid fraction, which elutes later in time. Illustratively, for DEAE cellulose chromatographic supports, the folic acid fraction has been observed to elute prior in time to the pteroic acid fraction, which elutes later in time. However, it is to be understood that for different chromatographic supports, including different saccharide-based chromatographic supports, it is contemplated herein that the order of elution of the first and second fractions as described herein may change.

In another embodiment, the methods described herein include the steps of (a) contacting a solution comprising pteroic acid, derivatives of pteroic acid, or combinations thereof, with an anion exchange chromatographic support; and (b) eluting a first fraction comprising pteroic acid, derivatives of pteroic acid, or combinations thereof.

In one variation, the eluting step includes a mobile phase having a pH of about 11 or greater, or a pH of about 11.5 or greater. In another variation, the pH is in the range from about 11 to about 13. The pH of the mobile phase may be adjusted or obtained by the addition of a wide variety of bases, including but not limited to NaOH, KOH, $Na_2CO_3$, $NaHCO_3$, $KHCO_3$, $K_2CO_3$, $NH_4OH$, and the like.

In one aspect, chromatographic supports for the chromatography methods described herein include but are not limited to ion-exchange resins, anion-exchange resins, saccharide-based resins, saccharide-based ion-exchange resins, saccharide-based anion-exchange resins, and the like. Saccharide-based chromatographic supports include one or more cellulose, amylose, agarose, sepharose, and sephadex resins, and combinations thereof. In another aspect, saccharide-based chromatographic supports include ion-exchange resins, such as an anionic exchange resins and cationic exchange resins. Illustrative saccharide-based ion-exchange resins include diethylaminoethyl (DEAE) cellulose or quaternary amine (QA) cellulose solid supports, such as DE23, DE32, DE51, DE52, DE53, and QA52, each available from Whatman and/or Sigma. In one illustrative variation, the chromatographic support is a pre-swollen microgranular DE52 anion exchanger (Whatman Cat. No. 4057-200). In another illustrative variation, the chromatographic support is a pre-swollen microgranular DE32 anion exchanger. Additional solid supports include DEAE Sephadex, CM Sephadex, Sephadex QA, Sepharose QA, and the like.

In another embodiment, the mobile phase is a reverse phase mobile phase comprising water. In another embodiment, the mobile phase is a reverse phase mobile phase comprising water and a salt. In another embodiment, the mobile phase is a reverse phase mobile phase comprising water and an organic solvent. In another embodiment, the mobile phase is a reverse phase mobile phase comprising water, a salt, and an organic solvent. In another aspect, the mobile phase is substantially free or completely free of ammonia, or salts thereof.

In another embodiment, the mobile phase is a reverse phase mobile phase comprising water at a specified pH, including a neutral or near neutral pH. In one variation, the pH is slightly above neutrality, such as a pH in the range from about 7.1 to about 7.7. In one aspect, the pH of the mobile phase is in the range from about 7.3 to about 7.5, or at a pH of about 7.4. In another embodiment, the mobile phase is a reverse phase mobile phase comprising water and a salt. In another embodiment, the mobile phase is a reverse phase mobile phase comprising water and an organic solvent. In another embodiment, the mobile phase is a reverse phase mobile phase comprising water, a salt, and an organic solvent. In another aspect, the mobile phase is substantially free or completely free of ammonia, or salts thereof.

The chromatography profile may use the mobile phase at a fixed relative composition or in a varying relative composition, including, but not limited to, isocratic profiles, step functions, simple gradients, complex gradients, linear gradients, logarithmic gradients, combinations of such profiles, and the like.

In another embodiment, the mobile phases used in the methods described herein may also optionally include an organic solvent as a component, such as an acetone, tetrahydrofuran, acetonitrile, alcohols, including MeOH, EtOH, and the like, and others. When the mobile phase includes two components, such as the aqueous component having a basic pH and an organic solvent component, the mobile phase may be eluted through the chromatographic support in an isocratic mode, or in a gradient mode. It is appreciated that gradient modes may follow a wide variety of profiles, including linear, logarithmic, hyperbolic, parabolic, exponential, step, and combinations thereof.

In another embodiment, the eluent from the column chromatography is monitored by any conventional technique including, but not limited to, ultraviolet (UV) absorbance, fluorescence, refractive index (RI), liquid chromatography mass spectrometry (LCMS), tandem mass spectrometry (MS/MS), and the like. Illustratively, the eluent is divided into one or more fractions based on the monitoring, and the fractions containing the desired product and having a purity at or above a predetermined threshold are pooled. The pooled fractions are included in the precipitating step.

In another embodiment of the precipitating step, the pteroic acid, or analog or derivative thereof, contained in fractions or pooled fractions of the eluent is precipitated from the solution by lowering the pH of the solution to a pH of about 3.5 or less, about 3 or less, about 2.5 or less, or about 2 or less. The pH may be lowered by the addition of any variety of acids or any combination of acids capable of lowering the pH to about 3.5 or less, about 3 or less, about 2.5 or less, or about 2 or less. Illustrative acids include, but are not limited to, hydrochloric acid, hydrobromic acid, sulfuric acid and salts thereof, phosphoric acid and salts thereof, nitric acid, and the like.

In one aspect, the precipitated and/or purified pteroic acid or analog or derivative thereof is purified to about 95% purity or greater, about 96% purity or greater, about 97% purity or greater, about 98% purity or greater, about 99% purity or greater, or about 100% purity. In another aspect, the precipitated pteroic acid or analog or derivative thereof is substantially free of folic acid. The purity of the precipitated pteroic acid or analog or derivative thereof may be measured using any conventional technique, including various chromatography or spectroscopic techniques, such as high pressure or high performance liquid chromatography (HPLC), nuclear magnetic resonance spectroscopy, TLC, UV absorbance spectroscopy, fluorescence spectroscopy, and the like.

In another aspect, the precipitated or purified pteroic acid, pteroic acid analogs, and/or pteroic acid derivatives have purities understood as being substantially pure, or substantially purified from one or more undesired or unwanted components, impurities, or contaminants. Illustratively, the purity of these compounds may be understood as having less than a percentage of one or more components, such as about 5% or less of an impurity, about 4% or less of an impurity, about 3% or less of an impurity, about 2% or less of an impurity, or about 1% or less of an impurity. Similarly, the purity of these compounds may be understood as having less than a percentage of a specific component, such as about 5% or less, about 4% or less, about 3% or less, about 2% or less, or about 1% or less of folic acid.

In another embodiment, pteroic acid, pteroic acid analogs, and pteroic acid derivatives are prepared by synthetic methods described herein. These synthetic methods result in compounds that have high overall percentage purities, such as about 95% pure or greater, about 96% pure or greater, about 97% pure or greater, about 98% pure of greater, about 99% pure or greater, or about 100% pure. Similarly, the purity of such pteroic acid, pteroic acid analogs, and pteroic acid derivatives are prepared by synthetic methods described herein may be understood as having less than a percentage of a specific component, such as about 5% or less, about 4% or less, about 3% or less, about 2% or less, or about 1% or less of folic acid, as a result of the synthetic method used, alone or in combination with a purification method described herein.

It is appreciated that specific components in the resulting pteroic acid, pteroic acid analog, pteroic acid derivative, or combination thereof may be either avoided or removed. Those components may be avoided by using the synthetic processes described herein. In addition, those components may be removed by using the purification methods described herein. Therefore, it is to be understood that the invention also includes materials that are prepared by the synthetic processes described herein, are produced from or result from use of the purification methods described herein, or result from a combination of these synthetic processes and purification methods.

In one embodiment, the pteroic acid or the derivative of pteroic acid is derived from a degradation process, such as a degradation of a folic acid or a derivative of folic acid. In one aspect, the pteroic acid or the derivative of pteroic acid is derived from an enzymatic degradation process, such as an enzymatic degradation of a folic acid or a derivative of folic acid. In another aspect, the pteroic acid or the derivative of pteroic acid is derived from a microbial degradation process, such as a microbial degradation of a folic acid or a derivative of folic acid. In another aspect, the pteroic acid or the derivative of pteroic acid is derived from a chemical degradation process, such as a chemical degradation of a folic acid or a derivative of folic acid. In another embodiment, the pteroic acid or the derivative of pteroic acid is derived from a chemical synthesis.

In one embodiment of the microbial degradation processes, folic acid or derivatives thereof are hydrolyzed to pteroic acid by contacting a sample of the folic acid or derivative thereof with *Alcaligenes faecalis*, Psuedomonad, Psuedomonad ATCC 25301, *flavobacterium, flavobacterium baccalis*, and the like. Illustrative conditions for performing microbial degradation of folic acid are described by Houlihan et al., *Anal. Biochem.*, 46:1-6 (1972), Pratt et al., *J. Biol. Chem.*, 243:6367 (1968); Levy et al., *J. Biol. Chem.*, 242:2933 (1967); Scott, *Methods in Enzymology*, 66:657-60 (1980); Lemon et al., "Conversion of pterolyglutamic acid to pteroic acid by bacterial degradation" *Archives of Biochemistry* 19:311-16 (1948), the disclosures of which are incorporated herein by reference.

In one embodiment of the enzymatic degradation processes, folic acid or derivatives thereof are hydrolyzed to pteroic acid by contacting a sample of the folic acid or derivative thereof with one or more enzymes such as carboxypeptidases, including carboxypeptidase G, carboxypeptidase A, amidases, lipases, esterases, and proteases, and combinations thereof. In the case of carboxypeptidase G, folic acid is contacted with the enzyme at slightly basic pH, illustratively a pH of about 7.3. Illustrative conditions for performing enzymatic degradation of folic acid is described by Harvison & Kalman, J. Med. Chem. 35:1227-33 (1992); Nomura et al., *J. Org. Chem.*, 65:5016-21 (2000); U.S. Pat. No. 4,337,339, the disclosures of which are incorporated herein by reference.

In one embodiment of the chemical degradation processes, folic acid or derivatives thereof are hydrolyzed to pteroic acid by contacting a sample of the folic acid or derivative thereof under acid or basic hydrolysis, or saponification conditions, generally in an aqueous medium, optionally supplemented with a miscible organic cosolvent.

In another embodiment, the pteroic acid, or analog or derivative of pteroic acid that is purified using the methods described herein is one resulting from a conventional degradation or synthetic process and is contaminated with a folic acid, or analog or derivative thereof. Illustratively, enzymatic degradation processes that convert folic acids, or analogs or derivatives thereof, to pteroic acids, or the corresponding analogs or derivatives thereof, may not proceed to complete conversion. Therefore, the resulting mixture may include the pteroic acid or derivative thereof, the folic acid or derivative thereof, and/or one or more partially degraded or hydrolyzed intermediate products or side products formed during the enzymatic degradation process or hydrolysis process. Illustratively, the relative amount of the folic acid or derivative thereof is in the range from about 1% to about 50%, or from about 1% to about 25%.

In one embodiment of a chemical synthesis of the pteroic acid or the derivative of pteroic acid, pteroic acid or a derivative or analog of pteroic acid, is coupled with another molecule to form a vitamin-drug conjugate. In one aspect, the vitamin-drug conjugate is illustratively a conjugate described in U.S. patent application Ser. No. 10/765,336. In another aspect, the vitamin-drug conjugate is illustratively a conjugate of pteroic acid, or an analog or derivative of pteroic acid, and an antigenic component, and includes the conjugates described in U.S. patent application Ser. No. 09/822,379, the disclosure of which is incorporated herein by reference.

In another aspect, the vitamin-drug conjugate may be described by the formula

V-L-D where V is a vitamin, or an analog or a derivative thereof, and L is an optional bivalent linker having a length of about 1 to about 100 atoms. The atoms are selected from carbon, nitrogen, oxygen, silicon, phosphorus, sulfur, and the like. Each of these atoms is optionally substituted with hydrogen, halogen, and/or one or more functional groups. Illustrative functional groups include, but are not limited to, hydroxy, cyano, nitro, oxo, thiono, optionally substituted imino, optionally substituted hydroxylimino, optionally substituted hydrazino, azido, optionally substituted alkyl, optionally substituted alkenyl, optionally substituted alkynyl, optionally substituted alkoxy, optionally substituted alkylthio, optionally substituted alkylsulfonyl, optionally substituted alkylsulfonyloxy, optionally substituted alkylsulfonylamino, optionally substituted amino, optionally substituted aldehydes and derivatives thereof, optionally substituted ketones and derivatives thereof, carboxylic acids and derivatives thereof, optionally substituted aryl, side chains of amino acids, peptides, combinations thereof, and the like. Such functional groups may be taken together to form cyclic structures attached to the atoms. Such functional groups may also be taken together to form cyclic structures with the atoms.

In another aspect, the vitamin-drug conjugate is a conjugate of pteroic acid or an analog or derivative thereof, and fluorescein or an analog or derivative thereof. In another aspect, the vitamin-drug conjugate is a compound of formula I (I)

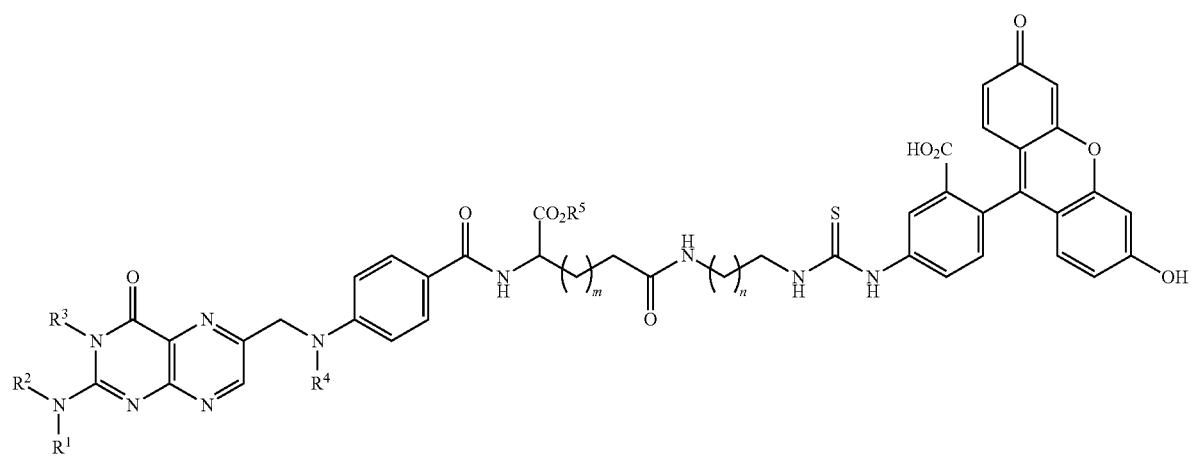

wherein $R^1$, $R^2$, $R^3$, and $R^4$ are each independently hydrogen, alkyl, acyl, or a suitably selected nitrogen protecting group, or $R^1$ and $R^2$ are taken together to form a nitrogen protecting group; $R^5$ is hydrogen, alkyl, or a suitably selected carboxyl protecting group; m is an integer from 0-4; and n is an integer from 1-4. In another aspect, the vitamin-drug conjugate is compound 8a (the compound of formula I, wherein $R^1$, $R^2$, $R^3$, $R^4$, and $R^5$ are hydrogen, m is 1, and n is 1).

One illustrative chemical synthesis of fluorescein conjugates of pteroic acid, and derivatives thereof, is shown in Scheme 1.

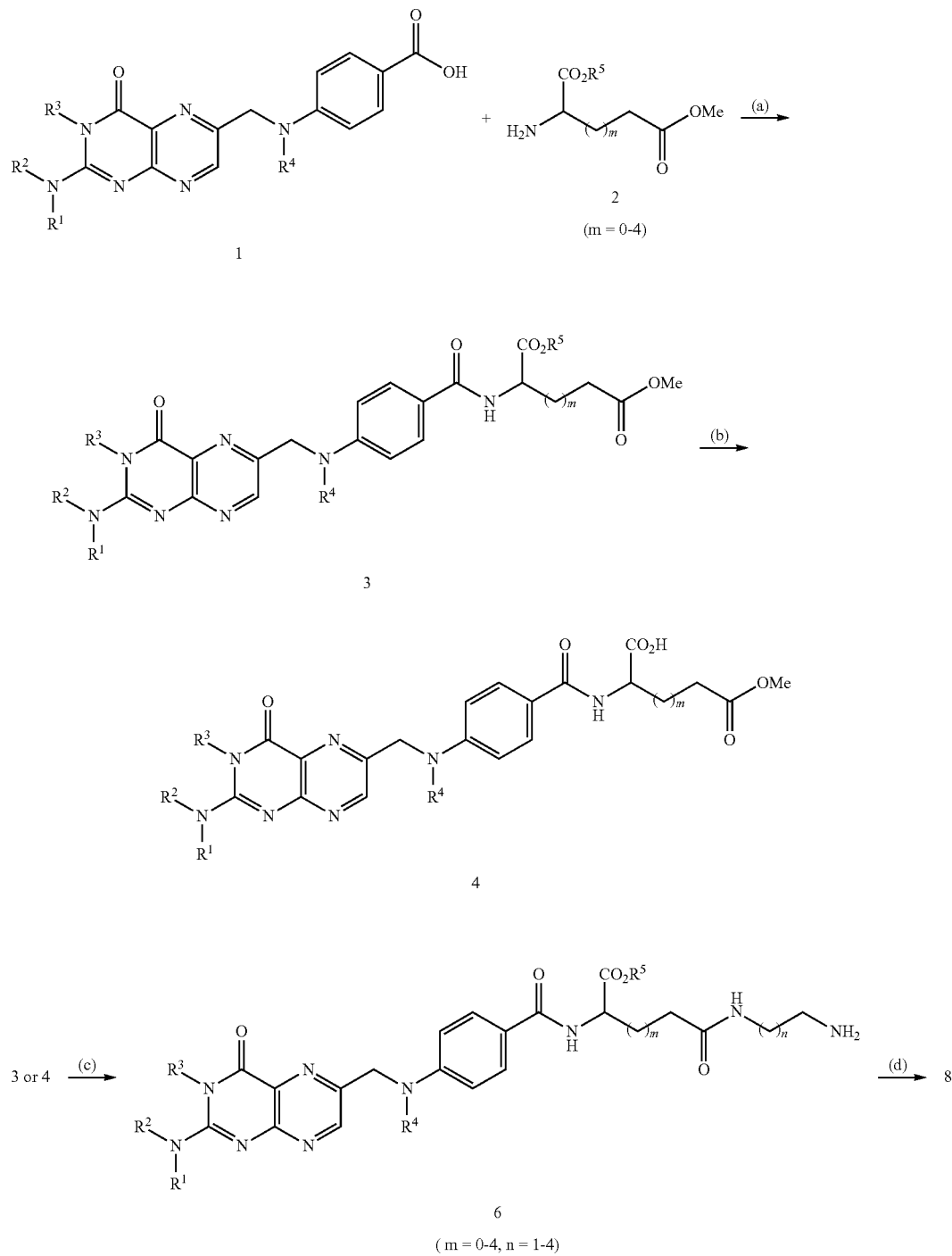

(a) amide coupling reagent; (b) selective deprotection of α-carboxyl group; (c) $H_2NCH_2(CH_2)_nNH_2$, n=1-4 (5); (d) 1. FITC (7); 2. optional deprotection of any of $R^1$ to $R^5$.

where $R^1$, $R^2$, $R^3$, and $R^4$ are each independently hydrogen, alkyl, acyl, or a suitably selected nitrogen protecting group, or $R^1$ and $R^2$ are taken together to form a nitrogen protecting group; $R^5$ is hydrogen, alkyl, or a suitably selected carboxyl protecting group; m is an integer from 0-4; and n is an integer from 1-4.

Protected pteroic acid analog 1 is reacted with protected amino acid analog 2 to form amide 3. Suitable protecting groups $R^1$, $R^2$, $R^3$, and $R^4$ for pteroic acid 1 include amide protecting groups, such as acetyl, trifluoroacetyl, and the like, carbamate protecting groups, such as tert-Boc, Teoc, Cbz, Fmoc, and the like, and others. Suitable protecting groups $R^5$ for amino acid analog 2 include ester protecting groups, such as methyl, trimethylsilylethyl, tert-butyl, and the like, and others. In one aspect, where $R^5$ is tert-butyl, resulting amide 3 is selectively deprotected with acid to give amide 4. It is appreciated that is this aspect, the protecting groups present on pteroic acid analog 1 and amino acid analog 2 are suitably selected to allow the selective deprotection of the α-carboxylate protecting group in the presence of the γ-carboxylate protecting group.

Either amide 3 or the corresponding deprotected analog 4 is treated with an alkylene diamine of the formula $H_2NCH_2(CH_2)_nNH_2$, where n=1-4 to give amine 6. The terminal methyl ester is displaced to form an amide bond. Amine 6 is treated with fluorescein isothiocyanate (FITC, 7) to form vitamin-drug conjugate 8.

A wide variety of amide coupling reagents and conditions are applicable to the syntheses described herein, including but not limited to carboxylic acid derivatives, such as acid chlorides and the like; activated esters, such as pentafluorophenyl esters, hydroxybenzotriazole esters, and the like; coupling reagents, such as (benzotriazol-1-yloxy)tripyrrolidinophosphonium hexafluorophosphate (PyBOP), BOP, BOPCl, DCC, EDC, HBTU, TBTU, PyBrOP, and the like. Suitable solvents for the amide coupling steps described herein include but are not limited to N,N-dimethylformamide (DMF), dimethylsulfoxide (DMSO), chloroform, dichloromethane (DCM), N-methylpyrrolidinone (NMP), and the like. The amide coupling steps described herein may be performed at many temperatures, such as temperatures in the range from about 0° C. to about 50° C., and illustratively at ambient temperature.

The deprotecting steps described herein may be performed in any conventional manner, such as using the reagents and reaction conditions described in Greene & Wuts "Protective Groups in Organic Synthesis," 2d Ed., John Wiley & Sons, New York, 1991, the disclosure of which is incorporated herein by reference. It is appreciated that the choice of deprotecting reagents and conditions is made to allow the deprotecting step to proceed without unintentionally affecting other functional groups, including other protecting groups, present on the compounds being deprotected. For example, in Scheme 1, protecting group $R^5$ is removed in the presence of and without affecting protecting group $R^4$. In one illustrative embodiment, protecting group $R^5$ is a tert-butyl ester, and protecting group $R^4$ is a trifluoroacetyl amide. Illustrative deprotecting agents for deprotecting acid sensitive protecting groups include but are not limited to trifluoroacetic acid (TFA), HCl, HBr, AcOH, $HCO_2H$, and the like. The deprotecting reaction may be performed in a variety of solvents, including but not limited to water, DCM, EtOAc, AcOH, and the like. It is appreciated that cation scavengers may also be included in the reaction conditions to improve the rate and/or overall yield of the deprotecting reactions, including with the use of AcOH as a solvent. The deprotecting reactions described herein may be performed at a variety of temperatures, such as temperatures in the range from about 0° C. to about 50° C., and illustratively at ambient temperature.

Step (c) in Scheme 1 may be performed in a variety of solvents, including but not limited to THF, ether, DMF, DMSO, chloroform, DCM, NMP, and the like, and may be performed at a variety of temperatures, such as temperatures in the range from about 0° C. to about 50° C., and illustratively at ambient temperature. Similarly, step (d) in Scheme 1 may be performed in a variety of solvents, including but not limited to THF, DMF, DMSO, chloroform, $CH_2Cl_2$, NMP, water, and the like, and may be performed at a variety of temperatures, such as temperatures in the range from about 0° C. to about 50° C., and illustratively at ambient temperature. Additional bases may be added to the reaction illustrated in step (d), including but not limited to amine bases generally represented by $R^1R^2R^3N$, $Et_3N$, N,N-diisopropylethylamine (DIPEA), pyridine, lutidine, collidine, 4-dimethylaminopyridine (DMAP), and the like.

It is appreciated that certain protecting groups may be contemporaneously and conveniently removed during step (c) upon reaction with the diamine $H_2NCH_2(CH_2)_nNH_2$. For example, when $R^4$ is an amide protecting group, such as trifluoroacetyl and the like, both the methyl ester is replaced to form the amide of the gamma-glutamate, and the amide protecting group is removed at N(10). In one variation, the group $R^4$ is selected to be stable to reaction with diamine $H_2NCH_2(CH_2)_nNH_2$.

In another variation, the reaction of pteroic acid analog 1 and amino acid analog 2 is accomplished by converting protected pteroic acid analog 1 to a corresponding carboxylic acid derivative having a leaving group. The leaving group is displaced by the amine of amino acid analog 2 to form amide 3. It is appreciated that the synthesis shown in Scheme 1, and variations thereof, may also be used to prepare fluorescein conjugates of pteroic acid analogs, and derivatives of pteroic acid analogs, as described herein.

Another illustrative chemical synthesis of conjugates of pteroic acid, and derivatives thereof, is shown in Scheme 2.

Scheme 2

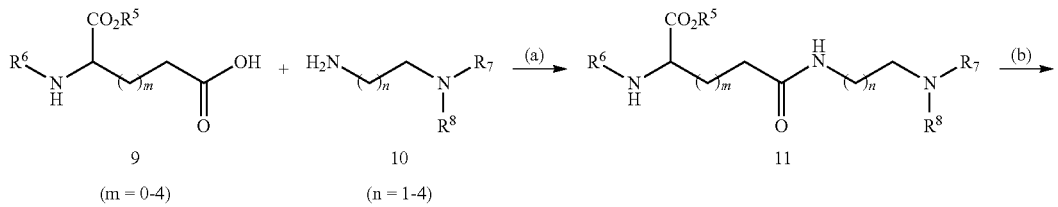

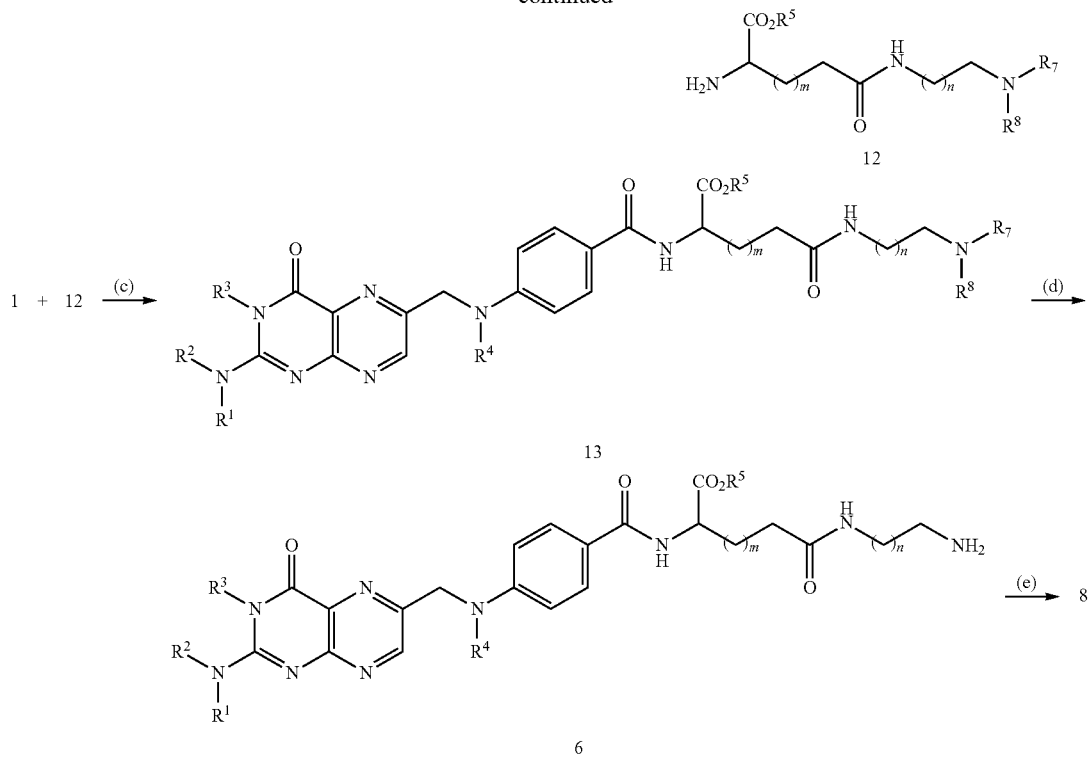

(a) amide coupling reagent; (b) selective deprotection of amino acid amine group; (c) amide coupling reagent; (d) selective deprotection of alkylene diamine; (e) 1. FITC (7); 2. optional deprotection of any of $R^1$ to $R^5$.
where R1, $R^2$, $R^3$, and $R^4$ are each independently hydrogen, alkyl, acyl, or a suitably selected nitrogen protecting group; $R^5$ is hydrogen, alkyl, or a suitably selected carboxyl protecting group; m is an integer from 0-4; n is an integer from 1-4; and $R^6$, $R^7$, and $R^8$ are each independently hydrogen or a suitably selected nitrogen protecting group.

Protected amino acid analog 9 is reacted with protected alkylenediamine 10 to form amide 11. Illustrative protecting groups $R^6$ for amino acid analog 7 include Fmoc, Cbz, tert-Boc, and the like. Illustrative protecting groups $R^7$ for alkylenediamine 10 include tert-Boc, Fmoc, Cbz, and the like. It is appreciated that the protecting groups are chosen to allow for the selective removal of one or more in the presence of the remaining protecting groups, and without altering the nature of the other functional groups remaining on the molecule being deprotected. Resulting amide 11 is deprotected to give amino acid amine 12, which is coupled with protected pteroic acid analog 1, where illustrative protecting groups $R^4$ for pteroic acid analog 1 are as described herein, to form amide 13. Resulting amide 13 is deprotected to give alkylenediamine amine 6. In some variations, depending upon the nature of the carboxyl protecting group $R^5$, the conditions used to remove the terminal amine protection groups $R^7$ and $R^8$ may also remove the carboxyl protection group $R^5$. For example, when $R^5$ is a tert-butyl group, $R^7$ is a tert-Boc protection group, and $R^8$ is hydrogen, treatment with acid in a dipolar solvent may remove both protecting groups. Amine 6 is reacted with FITC to give pteroic acid-linked FITC conjugate 8.

As described herein, a wide variety of amide coupling reagents and conditions are also applicable to the synthesis described in Scheme 2, including but not limited to carboxylic acid derivatives, such as acid chlorides and the like; activated esters, such as pentafluorophenyl esters, hydroxybenzotriazole esters, and the like; coupling reagents, such as PyBOP, BOP, BOPCl, DCC, EDC, HBTU, TBTU, PyBrOP, and the like. Suitable solvents for the amide coupling steps described herein include but are not limited to DMF, DMSO, chloroform, $CH_2Cl_2$, NMP, and the like. The amide coupling steps described herein may be performed at many temperatures, such as temperatures in the range from about 0° C. to about 50° C., and illustratively at ambient temperature.

The deprotecting steps described herein may be performed in any conventional manner, such as using the reagents and reaction conditions described in Greene & Wuts. It is appreciated that the choice of deprotecting reagents and conditions is made to allow the deprotecting step to proceed without unintentionally affecting other functional groups, including other protecting groups, present on the compounds being deprotected. For example, in Scheme 2, protecting group $R^6$ is removed in the presence of and without affecting protecting groups $R^5$, $R^7$, and $R^8$. In one illustrative embodiment, protecting group $R^6$ is a Fmoc group, and protecting group $R^5$ is a tert-Bu ester, protecting group $R^7$ is a tert-Boc, and $R^8$ is hydrogen. Illustrative deprotecting agents for deprotecting base sensitive protecting groups include but are not limited to DBU, peperidine, morpholine, TBAF, and the like. The deprotecting reaction may be performed in a variety of solvents, including but not limited to water, THF, ether, DMF, NMP, $CH_2Cl_2$, EtOAc, and the like. The deprotecting reactions described herein may be performed at a variety of temperatures, such as temperatures in the range from about 0° C. to about 50° C., and illustratively at ambient temperature.

Coupling step (c) in Scheme 2 may be performed in similarly to that in step (a), with the coupling agents, and reaction conditions, described herein. A variety of solvents, including but not limited to THF, ether, DMF, DMSO, chloroform, CH$_2$Cl$_2$, NMP, and the like, and may be performed at a variety of temperatures, such as temperatures in the range from about 0° C. to about 50° C., and illustratively at ambient temperature. Similarly, step (d) in Scheme 1 may be performed in a variety of solvents, including but not limited to THF, DMF, DMSO, chloroform, CH$_2$Cl$_2$, NMP, water, and the like, and may be performed at a variety of temperatures, such as temperatures in the range from about 0° C. to about 50° C., and illustratively at ambient temperature. Additional bases may be added to the reaction illustrated in step (d), including but not limited to amine bases generally represented by R$^1$R$^2$R$^3$N, Et$_3$N, DIPEA, pyridine, lutidine, collidine, DMAP, and the like.

Deprotecting step (d) may be performed in any conventional manner. In one illustrative embodiment, protecting group R$^7$ is a tert-Boc group, which is chemically sensitive to acid, whereas the other protecting groups are not, such as R$^4$ as a trifluoroacetyl amide, or R$^5$ as a methyl ester. In another illustrative embodiment, protecting group R$^5$ is a tert-butyl ester and protecting group R$^7$ is a tert-Boc group, which are both chemically sensitive to acid, whereas the other protecting groups are not. Illustrative deprotecting agents for deprotecting such acid sensitive protecting groups include but are not limited to TFA, HCl, HBr, AcOH, HCO$_2$H, and the like. The deprotecting reaction may be performed in a variety of solvents, including but not limited to water, CH$_2$Cl$_2$, EtOAc, AcOH, and the like. It is appreciated that cation scavengers may also be included in the reaction conditions to improve the rate and/or overall yield of the deprotecting reactions, including with the use of AcOH as a solvent. The deprotecting reactions described herein may be performed at a variety of temperatures, such as temperatures in the range from about 0° C. to about 50° C., and illustratively at ambient temperature.

Optional deprotecting step (e) may be included in the synthesis described in Scheme 2 to remove any remaining protecting groups on the compounds 8. For example, when R$^4$ is an amide protecting group and R$^5$ is a carboxylic acid protecting group, such groups may be removed to prepare the free amino acid derivative illustrated by compound 8. In one illustrative embodiment, coupling step (e) in Scheme 2 gives a protected form of compound 8, where R$^1$, R$^2$, R$^3$, and R$^5$ are hydrogen, and R$^4$ is trifluoroacetyl. Protecting group R$^5$ may be contemporaneously removed by contacting the protected compound 8 with a base, including but not limited to NH$_4$OH, including 0.5 M NH$_4$OH, LiOH, NaOH, KOH, K$_2$CO$_3$, NaHCO$_3$, and the like, in a variety of solvents, including but not limited to water, alcohols, biphasic THF/water, and the like. Illustratively, the pH of the reaction conditions for removing such base sensitive protecting groups is greater than about 9. The reaction is illustratively performed at ambient temperature.

Another illustrative chemical synthesis of fluorescein conjugates of pteroic acid, and derivatives thereof, is shown in Scheme 3.

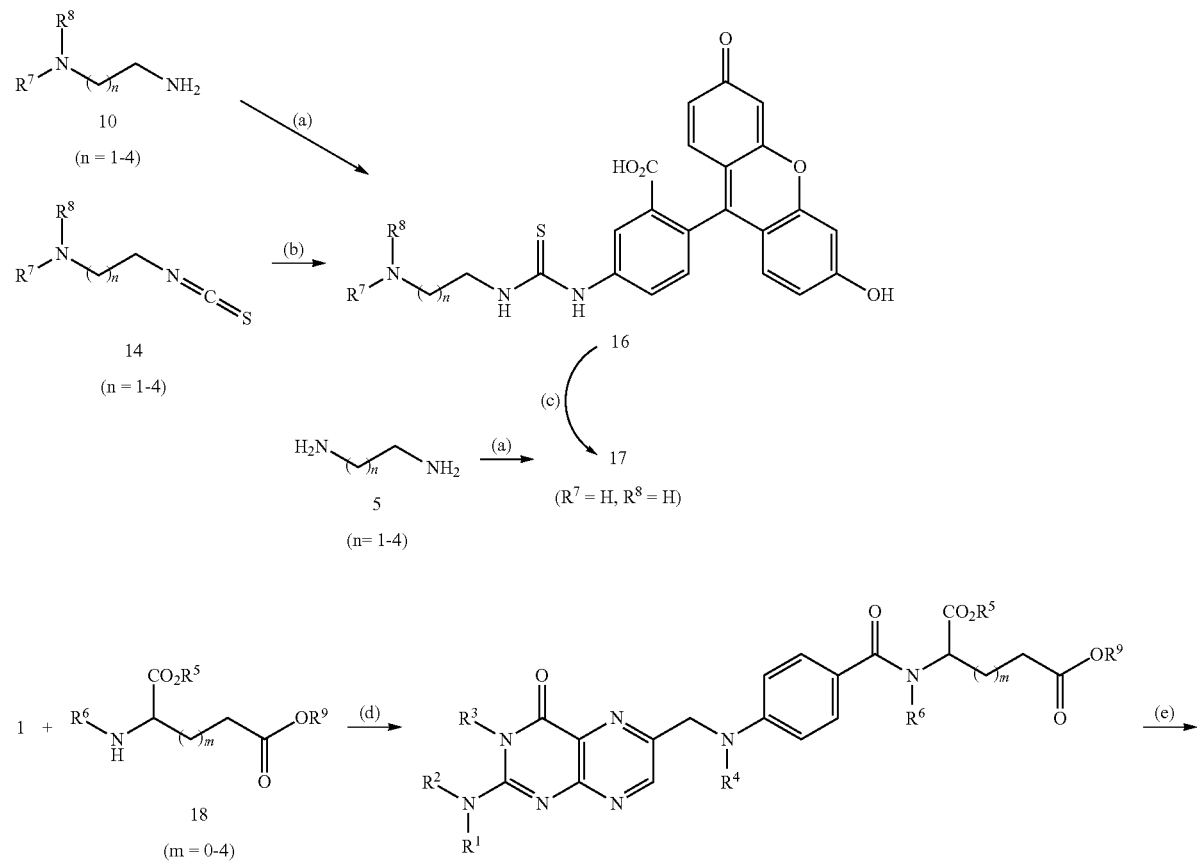

Scheme 3

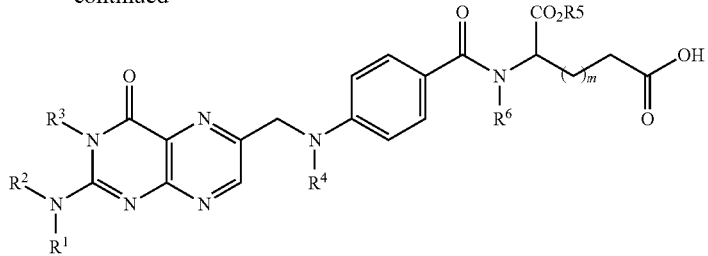

20

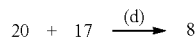

(a) FITC (7); (b) fluorescein-$NH_2$ (15); (c) deprotection of amine group; (d) amide coupling reagent; (e) selective deprotection of carboxylic acid group; (f) 1. amide coupling reagent; 2. optional deprotection of any of $R^1$ to $R^6$. where $R^1$, $R^2$, $R^3$, and $R^4$ are each independently hydrogen, alkyl, acyl, or a suitably selected nitrogen protecting group; $R^5$ is hydrogen, alkyl, or a suitably selected carboxyl protecting group; $R^9$ is hydrogen, alkyl, or a suitably selected carboxyl protecting group; m is an integer from 0-4; n is an integer from 1-4; and $R^6$, $R^7$, and $R^8$ are each independently hydrogen or a suitably selected nitrogen protecting group.

Protected alkylene diamine 16 may be prepared by either (i) reacting alkylene diamine 5 with FITC (7); (ii) reacting protected alkylene diamine 10 with FITC (7); or (iii) reacting protected aminoalkyl isothiocyanate 14 with fluoresceinamine (15). The amine is deprotected to give 17. Pteroic acid derivative 1 is coupled with triply protected amino acid 18 to give folic acid derivative 19. The protecting groups $R^5$ and $R^9$ are selected so that each may be chemically removed independent of the other. Protecting group $R^9$ is removed to give carboxylic acid 20, which is coupled to amine 17 to give conjugate 8.

The reaction of isothiocyanates with amines, as illustrated in Scheme 3 for the reaction of compounds 5, 10, 14 with compounds 7 and 15, as appropriate, may be performed in a variety of solvents, including but not limited to EtOH, MeOH, THF, $CH_2Cl_2$, DMF, $CHCl_3$, and the like. The reactions may be performed at a variety of temperatures, such as temperatures in the range from about 0° C. to about 100° C., and illustratively at reflux for the solvent sued in the reaction.

Similarly to the deprotecting reactions described herein, deprotecting step (c) may be performed in any conventional manner. In one illustrative embodiment, protecting group $R^7$ is a tert-Boc group, which is chemically sensitive to acid. Illustrative deprotecting agents for deprotecting such acid sensitive protecting groups include but are not limited to TFA, HCl, HBr, AcOH, $HCO_2H$, and the like. The deprotecting reaction may be performed in a variety of solvents, including but not limited to water, $CH_2Cl_2$, EtOAc, AcOH, and the like. It is appreciated that cation scavengers may also be included in the reaction conditions to improve the rate and/or overall yield of the deprotecting reactions, including with the use of AcOH as a solvent. The deprotecting reactions described herein may be performed at a variety of temperatures, such as temperatures in the range from about 0° C. to about 50° C., and illustratively at ambient temperature.

The coupling steps (d) and (f) in Scheme 3 may be performed in similarly to that described herein, with conventional coupling agents, and reaction conditions. A variety of solvents, including but not limited to THF, ether, DMF, DMSO, chloroform, $CH_2Cl_2$, NMP, and the like, and may be performed at a variety of temperatures, such as temperatures in the range from about 0° C. to about 50° C., and illustratively at ambient temperature.

Similarly to the deprotecting reactions described herein, deprotecting step (e) may be performed in any conventional manner. In one illustrative embodiment, protecting group $R^9$ is a tert-Bu ester, which is chemically sensitive to acid. Illustrative deprotecting agents for deprotecting such acid sensitive protecting groups include but are not limited to TFA, HCl, HBr, AcOH, $HCO_2H$, and the like. The deprotecting reaction may be performed in a variety of solvents, including but not limited to water, $CH_2Cl_2$, EtOAc, AcOH, and the like. It is appreciated that cation scavengers may also be included in the reaction conditions to improve the rate and/or overall yield of the deprotecting reactions, including with the use of AcOH as a solvent. The deprotecting reactions described herein may be performed at a variety of temperatures, such as temperatures in the range from about 0° C. to about 50° C., and illustratively at ambient temperature.

Optional deprotecting step (f) may be included in the synthesis described in Scheme 3 to remove any remaining protecting groups on the compounds 8. For example, when $R^4$ is an amide protecting group and $R^5$ is a carboxylic acid protecting group, such groups may be removed to prepare the free amino acid derivative illustrated by compound 8. In one illustrative embodiment, coupling step (f) in Scheme 3 gives a protected form of compound 8, where $R^1$, $R^2$, and $R^3$ are hydrogen, $R^4$ is trifluoroacetyl, and $R^5$ is methyl. Protecting groups $R^4$ and $R^5$ may be contemporaneously removed by contacting the protected compound 8 with a base, including but not limited to $NH_4OH$, including 0.5 M $NH_4OH$, LiOH, NaOH, KOH, $K_2CO_3$, and the like, in a variety of solvents, including but not limited to water, alcohols, biphasic THF/water, and the like. Illustratively, the pH of the reaction conditions for removing such base sensitive protecting groups is greater than about 9. The reaction is illustratively performed at ambient temperature.

Alternatively, illustrative chemical synthesis of fluorescein conjugates of pteroic acid, and derivatives thereof, is shown in Scheme 3a.

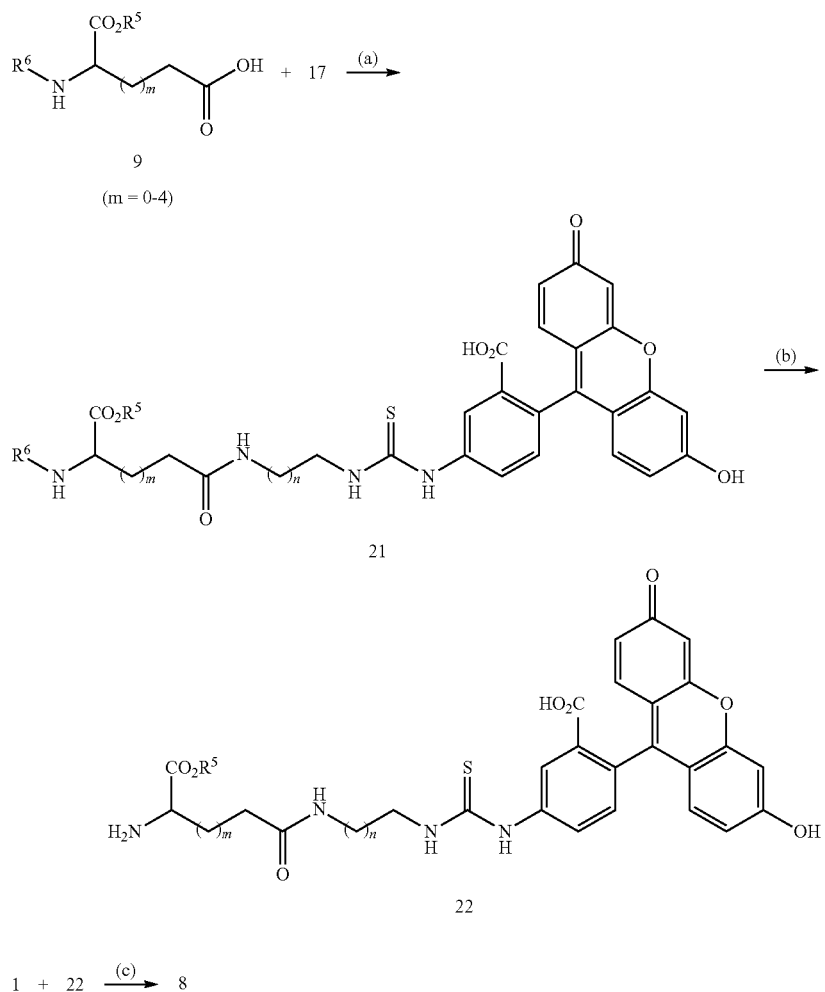

Scheme 3a (a) amide coupling reagent; (b) selective deprotection of amino acid amine group; (c) amide coupling reagent.

Amine 17 is coupled with protected amino acid analog 9 to give amide 21, as shown Amide 21 is deprotected to give amine 22, which is coupled with protected pteroic acid analog 1 to give vitamin-fluorescein conjugate 8.

It is appreciated that the syntheses shown in Schemes 1, 2, and 3, and variations thereof, may also be used to prepare fluorescein conjugates of pteroic acid analogs, and derivatives of pteroic acid analogs, as described herein. Pteroic acid analogs, and derivatives of pteroic acid analogs, include but are not limited to folinic acid, pteropolyglutamic acid, tetrahydropterins, dihydrofolates, tetrahydrofolates, aminopterin, amethopterin, $N^{10}$-methylfolate, 2-deaminohydroxyfolate, 3',5'-dichloro-4-amino-4-deoxy-$N^{10}$-methylpteroylglutamic acid, and the like, as well as deaza and dideaza analogs of these compounds, such as 1-deazamethopterin, 3-deazamethopterin, and other deaza and dideaza analogs, such as 1-deaza, 3-deaza, 5-deaza, 8-deaza, and 10-deaza analogs, and 1,5-dideaza, 5,10-dideaza, 8,10-dideaza, and 5,8-dideaza analogs. For example, other analogs of folate that include one or more amino acids in addition to or in place of glutamate may be prepared according to the processes and procedures described herein. Illustratively, in Schemes 1, 2, and 3, protected forms of tyrosine, cysteine, cysteic acid, phenylalanine, lysine, and many other natural and non-natural amino acids may be substituted for the protected glutamate compounds specifically described in those Schemes. Thus, folic acid analogs that differ from folate by being pteroyl amides of amino acids other than glutamate are contemplated herein. Further, it is to be understood that such amides may also be prepared from pteroic acid analogs and derivatives using the syntheses and processes described herein.

It is also appreciated that side products, contaminants, impurities, and/or other components may form during the preparation of the pteroic acid, folic acid, the analogs and derivatives of pteroic acid and folic acid, and conjugates of any of these compounds. These side products, contaminants, impurities, and/or other components may be removed by the purification methods described herein. In one embodiment, the other component is folic acid. In another embodiment, the other component is a bisfluorescein derivative, such as the bisfluorescein derivative. One illustrative bisfluorescein derivative is a compound of formula II

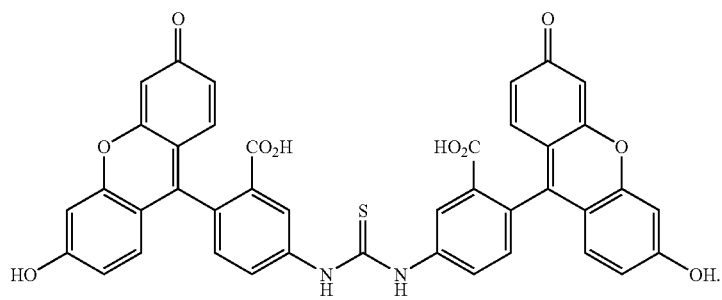

(II)

Another illustrative bisfluorescein derivative is a compound of formula III

FITC intermediate 16, as shown in Scheme 3, prior to conjugation with the pteroic acid, folic acid, or analog or derivative

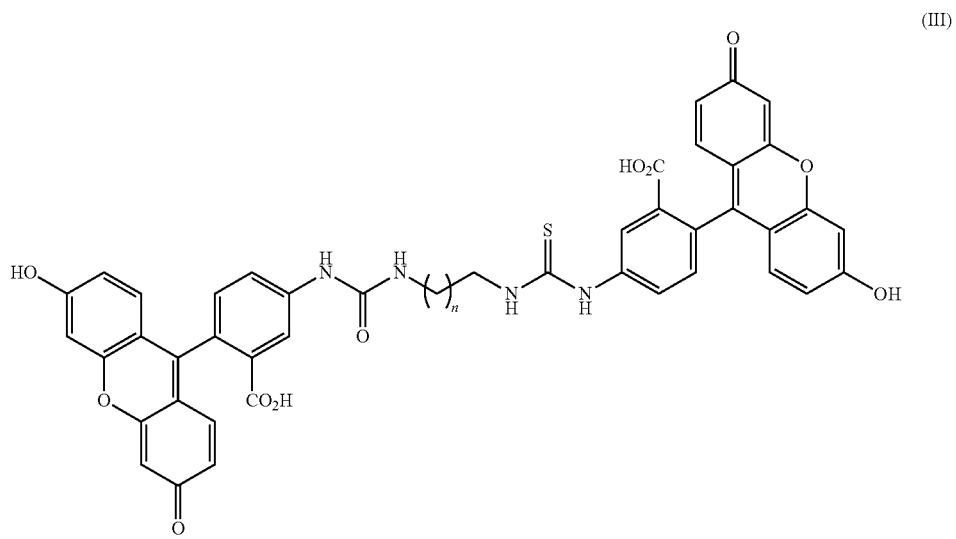

(III)

wherein n is an integer from 1-4.

It is also appreciated that side products, contaminants, or impurities may be avoided by selecting a suitable synthetic route, or modifying a synthetic route. In one illustrative aspect, the compound of formula II may be substantially or completely avoided by the careful elimination of water from the various synthetic methods and processes described herein. In another illustrative aspect, the compound of formula II may be avoided by using the FITC reagent in exactly one or slightly less than one molar equivalent.

In another illustrative aspect, the compound of formula III may be substantially or completely avoided by using the alkylene diamine reagent 5, in exactly one or slightly less than one molar equivalent, as shown in Scheme 1. In another illustrative aspect, the compound of formula III may be avoided by purifying the reaction products following the introduction of the alkylene diamine reagent 5 to substantially remove any remaining alkylene diamine reagent 5 prior to the addition of FITC, such as purifying the intermediate amine 6 shown in Scheme 1 to substantially or completely remove the alkylene diamine reagent 5.

In another illustrative aspect, the compound of formula III may be avoided by using a synthetic equivalent of the alkylene diamine, such as the monoprotected alkylene diamine 10, as shown in Scheme 2. In another illustrative aspect, the compound of formula III may be avoided by preparing the of pteroic acid or folic acid. In this latter aspect, it is appreciated that the compound of formula III may be avoided by using the alkylene diamine reagent, illustratively compound 5, in exactly at least a slight excess, or illustratively a substantial excess above one molar equivalent. It is also appreciated in this latter aspect, that the product compound 16, or subsequent products, such as 17, 21, or 22, when they are prepared from alkylene diamine reagent 5 may be purified to substantially or completely remove the compound of formula III.

Illustratively, a conjugate of pteroic acid, or a derivative thereof, can be synthesized by any of the methods described herein in combination with purification by any of the methods described herein employing an ion-exchange chromatographic support, such as those described herein.

In another embodiment, methods for purifying conjugates comprising pteroic acid or derivatives thereof, and fluorescein or derivatives thereof. In one aspect, the methods include the steps of (a) contacting a solution that includes the conjugate with a first reversed phase chromatographic support; (b) eluting a first fraction that includes a phosphate complex of the conjugate with a mobile phase, where the mobile phase includes water at a predetermined pH; (c) contacting the first fraction with a second reversed phase chromatographic support; and (d) eluting a second fraction that includes the conjugate with a mobile phase comprising water, where the second fraction is substantially free or completely free of phosphate. Eluting step (b) may be performed with an aqueous mobile phase prepared from water and one or more phosphate salts. The predetermined pH may be in the range from about 6 to about 8; in the range from about 7 to about 8; or in the range from about 7.1 to about 7.5, or illustratively at a pH of about 7.4. It is appreciated that eluting step (d) includes a mobile phase that is advantageously substantially or completely free of phosphate salts.

In one aspect, the reversed-phase chromatographic support is a modified silica support including, but not limited to, a C8 silica, a C18, silica, and modified C8 and/or C18 silicas, including capped or deactivated silicas, and the like, and combinations thereof.

It is appreciated that the chromatography column or columns described for use in the methods described herein may be regenerated using conventional techniques and then reused for the purification or separation of additional mixtures of pteroic acid, or analogs or derivatives thereof. Regeneration includes washing the chromatographic solid support with a solvent having a higher eluotropic index or eluotropic power than the mobile phase used for the separation. For example, a purification may include a reversed phase solid support and a mobile phase comprising water, such as pure water or an inorganic salt solution in water. The mobile phase may also include an organic solvent, such as acetonitrile (ACN), methanol, tetrahydrofuran (THF), and the like. In such an illustrative chromatographic separation, the mobile phase may be a fixed or variable mixture of water and acetonitrile, such as 90:10 water/acetonitrile, a linear gradient of 99:1 to 90:10 water/acetonitrile, and the like. Subsequently, the column may be illustratively regenerated by washing with a mobile phase having a higher eluotropic index that includes a higher percentage of the organic solvent relative to the percentage of water, such as 60:40 or 50:50 water/acetonitrile. These illustrative embodiments are not limiting and any suitable mobile phase mixture for chromatographic separation and any suitable method for column regeneration may be used.

In another illustrative embodiment, methods are described herein for purifying conjugates comprising pteroic acid or analogs or derivatives thereof, and fluorescein or derivatives thereof may be purified by complexation with a polyvalent cation, such as an alkaline earth metal cation. Illustrative cations include but are not limited to magnesium, calcium, beryllium, strontium, barium, and the like. Conventional methods are used to prepare salts such as sodium and/or potassium salts of the conjugates. Cation exchange is illustratively accomplished by mixing the sodium or potassium salt form with a polyvalent cation salt solution in a polar solvent, such as water. The polyvalent cation salt solution is prepared from conventional salts such as magnesium chloride, calcium chloride, and the like. The resulting complex is precipitated or crystallized from the polar solvent. It is appreciated that co-solvents may also be added to the polar solvent to facilitate precipitation of the polyvalent cation salts of the conjugates.

Polyvalent cation salts of the conjugates may be converted back to neutral forms or other salts forms, such as sodium and potassium salts by ion exchange chromatography on a suitable conventional resin.

In another illustrative embodiment, a method is provided for the therapeutic treatment of a host harboring a pathogenic cell population, such as cancer cells or pathogenic organisms. Illustratively, the method employs an isolated ligand-fluorescein conjugate capable of high affinity binding to cancer cells or other pathogenic agents. The method results in enhancement of the immune response-mediated elimination of pathogenic cell populations by rendering the pathogenic cells antigenic resulting in their recognition and elimination by the host immune system. In this method, the ligand-fluorescein conjugate is synthesized as described herein to avoid the formation of at least one bisfluorescein derivative and/or may be purified as described above to remove at least one bisfluorescein derivative.

In accordance with the methods and compositions described herein, the term "isolated ligand-fluorescein conjugate" refers to a ligand-fluorescein conjugate that has been purified or manipulated to remove at least one bisfluorescein derivative, or to a ligand-fluorescein conjugate that has been synthesized to avoid the formation of at least one bisfluorescein derivative, or to both.

In another illustrative embodiment, the method can utilize combination therapy by employing the isolated ligand-fluorescein conjugate, and an additional therapeutic factor capable of stimulating an endogenous immune response, a cell killing agent, a chemotherapeutic agent, a tumor penetration enhancer, a cytotoxic immune cell, or an antimicrobial agent to enhance immune response-mediated elimination of the pathogenic cell populations.

Illustratively, the method is utilized to enhance an endogenous immune response-mediated elimination of a population of pathogenic cells in a host animal harboring the population of pathogenic cells. The method is applicable to populations of pathogenic cells that cause a variety of pathologies such as cancer and infectious diseases. Thus, the population of pathogenic cells can be a cancer cell population that is tumorigenic, including benign tumors and malignant tumors, or it can be non-tumorigenic. The cancer cell population can arise spontaneously or by such processes as mutations present in the germline of the host animal or somatic mutations, or it can be chemically-, virally-, or radiation-induced. The method can be utilized to treat such cancers as carcinomas, sarcomas, lymphomas, Hodgekin's disease, melanomas, mesotheliomas, Burkitt's lymphoma, nasopharyngeal carcinomas, leukemias, and myelomas. The cancer cell population can include, but is not limited to, oral, thyroid, endocrine, skin, gastric, esophageal, laryngeal, pancreatic, colon, bladder, bone, ovarian, cervical, uterine, breast, testicular, prostate, rectal, kidney, liver, and lung cancers.

Illustratively, the population of pathogenic cells can also be an exogenous pathogen or a cell population harboring an exogenous pathogen, e.g., a virus. The method is applicable to such exogenous pathogens as bacteria, fungi, viruses, mycoplasma, and parasites. Infectious agents that can be treated with the method are any art-recognized infectious organisms that cause pathogenesis in an animal, including such organisms as bacteria that are gram-negative or gram-positive cocci or bacilli, DNA and RNA viruses, including, but not limited to, DNA viruses such as papilloma viruses, parvoviruses, adenoviruses, herpesviruses and vaccinia viruses, and RNA viruses, such as arenaviruses, coronaviruses, rhinoviruses, respiratory syncytial viruses, influenza viruses, picornaviruses, paramyxoviruses, reoviruses, retroviruses, and rhabdoviruses. Folate receptors have previously been identified on bacterial cells (Kumar et al., J. Biol. Chem. 262, 7171-79 (1987)).

Of interest are bacteria that are resistant to antibiotics such as antibiotic-resistant *Streptococcus* species and *Staphlococcus* species, or bacteria that are susceptible to antibiotics, but cause recurrent infections treated with antibiotics so that resistant organisms eventually develop. Such organisms can be treated with the isolated ligand-fluorescein conjugates in combination with lower doses of antibiotics than would normally be administered to a patient to avoid the development of these antibiotic-resistant bacterial strains. The method is also applicable to any fungi, mycoplasma species, parasites, or other infectious organisms that cause disease in animals. Examples of fungi that can be treated with the method of the present invention include fungi that grow as molds or are yeastlike, including, for example, fungi that cause diseases such as ringworm, histoplasmosis, blastomycosis, aspergillosis, cryptococcosis, sporotrichosis, coccidioidomycosis, paracoccidio-idomycosis, and candidiasis.

The method can also be utilized to treat parasitic infections including, but not limited to, infections caused by somatic tapeworms, blood flukes, tissue roundworms, ameba, and *Plasmodium, Trypanosoma, Leishmania,* and *Toxoplasma* species. Parasites of interest are those that express folate receptors and bind folate or pteroic acid, or derivatives of folate or pteroic acid.

Penicillins and cephalosporins known for their antibiotic activity and specific binding to bacterial cell wall precursors can also be used as ligands for preparing the isolated ligand-fluorescein conjugates for use in accordance with this method. The isolated ligand-fluorescein conjugates can be directed to a cell population harboring endogenous pathogens wherein pathogen-specific antigens are preferentially expressed on the surface of cells harboring the pathogens, and act as receptors for the ligand with the ligand specifically binding to the antigen.

Illustratively, the method can be used for both human clinical medicine and veterinary applications. Thus, the host animals harboring the population of pathogenic organisms and treated with the isolated ligand-fluorescein conjugates can be humans or, in the case of veterinary applications, can be a laboratory, agricultural, domestic, or wild animals. The method can be applied to host animals including, but not limited to, humans, laboratory animals such rodents (e.g., mice, rats, hamsters, etc.), rabbits, monkeys, chimpanzees, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

Illustratively, the isolated ligand-fluorescein conjugate is administered to the host animal parenterally, e.g., intradermally, subcutaneously, intramuscularly, intraperitoneally, or intravenously. In another embodiment, the conjugate can be administered to the host animal by other medically useful processes, and any effective dose and suitable therapeutic dosage form, including prolonged release dosage forms, can be used. The method can be used in combination with surgical removal of a tumor, radiation therapy, chemotherapy, or biological therapies such as other immunotherapies including, but not limited to, monoclonal antibody therapy, treatment with immunomodulatory agents, adoptive transfer of immune effector cells, treatment with hematopoietic growth factors, cytokines and vaccination.

Illustratively, suitable ligands include folic acid, analogs and derivatives of folic acid, and other folate receptor-binding molecules, including pteroic acid, and derivatives thereof, and other vitamins. Folate and pteroic acid derivatives include folate receptor-binding pteridines such as tetrahydropterins, dihydrofolates, tetrahydrofolates, and their deaza and dideaza analogs. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5 dideaza, 5,10-dideaza, 8,10-dideaza, and 5,8-dideaza analogs. The foregoing derivatives bind to folate-receptors. Other derivatives useful in the method described herein are the folate receptor-binding analogs aminopterin, amethopterin (methotrexate), $N^{10}$-methylfolate, 2-deamino-hydroxyfolate, deaza analogs such as 1-deazamethopterin or 3-deazamethopterin, and 3',5'-dichloro-4-amino-4-deoxy-$N^{10}$-methylpteroylglutamic acid (dichloromethotrexate).

Other suitable vitamins that can be used as ligands include niacin, pantothenic acid, riboflavin, thiamine, biotin, vitamin $B_{12}$, and the lipid soluble vitamins A, D, E and K. (See U.S. Pat. Nos. 5,108,921, 5,416,016, 5,635,382, and 5,688,488 incorporated herein by reference.) These vitamins, and their receptor-binding analogs and derivatives, constitute the ligand that can be coupled with fluorescein according to the procedures described herein.

Other suitable ligands include peptide ligands identified from library screens, tumor-specific peptides, tumor-specific aptamers, tumor-specific carbohydrates, tumor-specific monoclonal or polyclonal antibodies, Fab or scFv (i.e., a single chain variable region) fragments of antibodies such as, for example, an Fab fragment of an antibody directed to EphA2 or other proteins specifically expressed or uniquely accessible on metastatic cancer cells, small organic molecules derived from combinatorial libraries, growth factors, such as EGF, FGF, insulin, and insulin-like growth factors, and homologous polypeptides, somatostatin and its analogs, transferrin, lipoprotein complexes, bile salts, selectins, steroid hormones, Arg-Gly-Asp containing peptides, retinoids, various Galectins, γ-opioid receptor ligands, cholecystokinin A receptor ligands, ligands specific for angiotensin AT1 or AT2 receptors, peroxisome proliferator-activated receptor γ ligands, β-lactam antibiotics, small organic molecules including antimicrobial drugs, and other molecules that bind specifically to a receptor preferentially expressed on the surface of tumor cells or on an infectious organism, or fragments of any of these molecules.

Of interest in the case of ligands that bind to infectious organisms, are any molecules, such as antibiotics or other drugs, that are known in the art to preferentially bind to the microorganism. The method also applies to ligands which are molecules, such as antimicrobial drugs, designed to fit into the binding pocket of a particular receptor, based on the crystal structure of the receptor, or other cell surface protein, and wherein such receptors are preferentially expressed on the surface of tumors, bacteria, viruses, mycoplasma, fungi, parasites, or other pathogens. It is also contemplated that ligands binding to any tumor antigens or other molecules preferentially expressed on the surface of tumor cells can be utilized. The ligands should be capable of specifically eliminating a population of pathogenic cells in the host animal due to preferential expression of a receptor for the ligand, accessible for ligand binding, on the pathogenic cells. The use of combinations of isolated ligand-fluorescein conjugates to maximize elimination of the pathogenic cells is also contemplated.

Illustratively, the method described herein employs fluorescein, or derivatives thereof, as the immunogen. Fluorescein, and derivatives thereof, should be capable of eliciting antibody production in the host animal or should be capable of binding to passively administered antibodies. In one illustrative embodiment, the host animal can develop a novel immunity through immunization against the unnatural antigen (i.e., fluorescein). Active immunization involves multiple injections of the unnatural antigen scheduled outside of a normal vaccination regimen to induce the novel immunity. Thus, the isolated ligand-fluorescein conjugates can be used to direct a previously acquired humoral or cellular immunity to a population of pathogenic cells in the host animal for elimination of the foreign cells or pathogenic organisms.

In embodiments where the host animal develops a novel immunity through immunization against the unnatural antigen (i.e., fluorescein), the host animal can be preimmunized, to establish the novel immunity, with fluorescein linked to a carrier that renders fluorescein, a hapten, immunogenic. Any adjuvants known to the skilled artisan, such as Freund's adjuvant, saponin adjuvants, Alum™ (Pierce Chemical Co.), and the like, can also be administered with the carrier-fluorescein conjugate to enhance the novel immunity to fluorescein. Illustratively, carriers that can be used include keyhole limpet hemocyanin (KLH), haliotis tuberculata hemocyanin (HtH), inactivated diptheria toxin, inactivated tetanus toxoid, purified protein derivative (PPD) of *Mycobacterium tuberculosis*, bovine serum albumin (BSA), ovalbumin (OVA), g-globulins, thyroglobulin, peptide antigens, and synthetic carriers, such as poly-L-lysine, dendrimer, and liposomes.

The carrier (e.g., KLH or BSA) can be conjugated to fluorescein by using any art-recognized method of forming a complex. This can include covalent, ionic, or hydrogen bonding of the carrier to the fluorescein, either directly or indirectly via a linking group such as a divalent linker. The fluorescein-carrier conjugates are illustratively formed by covalent bonding through the formation of amide, ester or imino bonds between acid, aldehyde, hydroxy, amino, or hydrazo groups on the respective components of the conjugates. In embodiments where a linker is used, the linker can comprise about 1 to about 30 carbon atoms or about 2 to about 20 carbon atoms. Lower molecular weight linkers (i.e., those having an approximate molecular weight of about 20 to about 500) can be employed. Also, the linker can comprise an indirect means for associating the carrier with the fluorescein, such as by connection through intermediary linkers, spacer arms, or bridging molecules.

The carrier-fluorescein conjugates can be purified to remove at least one bisfluorescein contaminant by any method known to the skilled artisan. Illustratively, an ultrafiltration step can be used to remove bisfluorescein contaminants or impurities from the carrier-fluorescein conjugates. A pharmaceutical composition comprising these carriers-fluorescein conjugates purified from bisfluorescein contaminants is contemplated.

In another illustrative embodiment, antibodies directed against fluorescein can be administered to the host animal to establish a passive immunity. The antibodies can be natural antibodies collected from serum or monoclonal antibodies that may or may not be genetically engineered antibodies, including humanized antibodies. The utilization of a particular amount of an antibody reagent to develop a passive immunity, and the use of an isolated ligand-fluorescein conjugate wherein the passively administered antibodies are directed to fluorescein, provides the advantage of a standard set of reagents to be used in cases where a patient's induced antibody titer is not therapeutically useful. The passively administered antibodies can be "co-administered" with the isolated ligand-fluorescein conjugate and co-administration is defined as administration of antibodies at a time prior to, at the same time as, or at a time following administration of the isolated ligand-fluorescein conjugate.

The isolated ligand-fluorescein conjugates enhance an endogenous immune response-mediated elimination of a population of pathogenic cells. The endogenous immune response can include a humoral response, a cell-mediated immune response, and any other immune response endogenous to the host animal, including complement-mediated cell lysis, antibody-dependent cell-mediated cytoxicity (ADCC), antibody opsonization leading to phagocytosis, clustering of receptors upon antibody binding resulting in signaling of apoptosis, antiproliferation, or differentiation, and direct immune cell recognition of the delivered hapten. It is also contemplated that the endogenous immune response will employ the secretion of cytokines that regulate such processes as the multiplication and migration of immune cells. The endogenous immune response can include the participation of such immune cell types as B cells, T cells, including helper and cytotoxic T cells, macrophages, natural killer cells, neutrophils, LAK cells and the like.

It is contemplated that the induced antibodies, or passively administered antibodies will be redirected to the tumor cells or infectious organisms by preferential binding of the isolated ligand-fluorescein conjugates to these invading cells or organisms and that the pathogenic cells will be killed by complement-mediated lysis, ADCC, antibody-dependent phagocytosis, or antibody clustering of receptors. The cytotoxic process can also involve other types of immune responses, such as cell-mediated immunity, as well as secondary responses that arise when the attracted antigen-presenting cells phagocytose the unwanted cells and present natural tumor antigens or antigens of foreign pathogens to the immune system for elimination of the cells or organisms bearing the antigens.

At least one additional composition comprising a therapeutic factor can be administered to the host in combination with the above-detailed methodology, to enhance the endogenous immune response-mediated elimination of the population of pathogenic cells, or more than one additional therapeutic factor can be administered. The therapeutic factor can be selected from a compound capable of stimulating an endogenous immune response, a chemotherapeutic agent, an antimicrobial agent, or other therapeutic factor capable of complementing the efficacy of the administered isolated ligand-fluorescein conjugate. The method described herein can be performed by administering to the host, in addition to the above-described conjugates, compounds or compositions capable of stimulating an endogenous immune response including, but not limited to, cytokines or immune cell growth factors such as interleukins 1-18, stem cell factor, basic FGF, EGF, G-CSF, GM-CSF, FLK-2 ligand, HILDA, MIP-1α, TGF-α, TGF-β, M-CSF, IFN-α, IFN-β, IFN-γ, soluble CD23, LIF, and combinations thereof.

In one illustrative embodiment, therapeutically effective combinations of these cytokines can be used. Therapeutically effective combinations of these cytokines can also be used. In one embodiment, for example, therapeutically effective amounts of IL-2, for example, in amounts ranging from about 0.1 MIU/m$^2$/dose/day to about 60 MIU/m$^2$/dose/day in a multiple dose daily regimen, and IFN-α, for example, in amounts ranging from about 0.1 MIU/m$^2$/dose/day to about 10 MIU/m$^2$/dose/day in a multiple dose daily regimen, can be used (MIU=million international units; m$^2$=approximate body surface area of an average human). In another embodiment IL-12 and IFN-α are used in therapeutically effective amounts, and in yet another embodiment IL-15 and IFN-α are used in therapeutically effective amounts. In another embodiment, IL-2, IFN-α or IFN-γ, and GM-CSF are used in combination. The therapeutic factor(s) used, such as IL-2, IL-12, IL-15, IFN-α, IFN-γ, and GM-CSF, including combinations thereof, can activate natural killer cells and/or T cells. Alternatively, the therapeutic factor or combinations thereof, including an interleukin in combination with an interferon and GM-CSF, can activate other immune effector cells such as macrophages, B cells, neutrophils, NK cells, NKT cells, T cells, LAK cells, or the like. The use of any other effective combination of cytokines including combinations of other interleukins and interferons and colony stimulating factors is also contemplated.

Chemotherapeutic agents, which are cytotoxic themselves and can work to enhance tumor permeability, suitable for use in the method include adrenocorticoids, alkylating agents, antiandrogens, antiestrogens, androgens, estrogens, antimetabolites such as cytosine arabinoside, purine analogs, pyrimidine analogs, and methotrexate, busulfan, carboplatin, chlorambucil, cisplatin and other platinum compounds, tamoxiphen, taxol, cyclophosphamide, plant alkaloids, prednisone, hydroxyurea, teniposide, antibiotics such as mitomycin C and bleomycin, nitrogen mustards, nitrosureas, vincristine, vinblastine, inflammatory and proinflammatory agents, and any other art-recognized chemotherapeutic agent. Other therapeutic agents that can be administered adjuvant to the administration of the conjugates described herein, include penicillins, cephalosporins, vancomycin, erythromycin, clindamycin, rifampin, chloramphenicol, aminoglycosides, gentamicin, amphotericin B, acyclovir, trifluridine, ganciclovir, zidovudine, amantadine, ribavirin, and any other art-recognized antimicrobial compound.

In one illustrative embodiment, the elimination of the population of pathogenic cells comprises a reduction or elimination of tumor mass or of pathogenic organisms resulting in a therapeutic response. In the case of a tumor, the elimination can be an elimination of cells of the primary tumor or of cells that have metastasized or are in the process of dissociating from the primary tumor. A prophylactic treatment to prevent return of a tumor after its removal by any therapeutic approach including surgical removal of the tumor, radiation therapy, chemotherapy, or biological therapy is also contemplated. The prophylactic treatment can be an initial treatment with the isolated ligand-fluorescein conjugate, such as treatment in a multiple dose daily regimen, and/or can be an additional treatment or series of treatments after an interval of days or months following the initial treatments(s).

In another illustrative embodiment, pharmaceutical compositions are provided comprising an amount of an isolated ligand-fluorescein conjugate effective to "label" a population of pathogenic cells in a host animal for specific elimination by an endogenous immune response or by co-administered antibodies. In another embodiment, the composition further comprises an amount of an additional factor, effective to enhance the elimination of the pathogenic cells, selected from the group consisting of a cell killing agent, a tumor penetration enhancer, a chemotherapeutic agent, an antimicrobial agent, a cytotoxic immune cell, and a compound capable of stimulating an endogenous immune response. The pharmaceutical composition contains therapeutically effective amounts of the isolated ligand-fluorescein conjugate and the therapeutic factor and the factor can comprise a cytokine such as IL-2, IL-12, or IL-15, or combinations of cytokines, including IL-2, IL-12, or IL-15 and interferons such as IFN-αA or IFN-γ and combinations of interferons, interleukins, and colony stimulating factors, such as GM-CSF.

The unitary daily dosage of the isolated ligand-fluorescein conjugate can vary significantly depending on the host condition, the disease state being treated, its route of administration and tissue distribution, and the possibility of co-usage of other therapeutic treatments such as radiation therapy. The effective amount to be administered to a patient is based on body surface area, patient weight, and physician assessment of patient condition. An effective dose can range from about 1 ng/kg to about 1 mg/kg, from about 1 μg/1 g to about 500 μg/kg, or from about 1 μg/kg to about 100 μg/kg.

Any effective regimen for administering the isolated ligand-fluorescein conjugate and the therapeutic factor to redirect induced antibodies to the tumor cells or infectious organisms or to induce a humoral response to the fluorescein can be used. For example, the isolated ligand-fluorescein conjugate and therapeutic factor can be administered as single doses, or they can be divided and administered as a multiple-dose daily regimen. Further, a staggered regimen, for example, one to three days per week can be used as an alternative to daily treatment, and such intermittent or staggered daily regimen is considered to be equivalent to every day treatment. In one embodiment, the host is treated with multiple injections of the isolated ligand-fluorescein conjugate and the therapeutic factor to eliminate the population of pathogenic cells. In another embodiment, the host is injected multiple times (preferably about 2 up to about 50 times) with the isolated ligand-fluorescein conjugate, for example, at 12-72 hour intervals or at 48-72 hour intervals. Additional injections of the isolated ligand-fluorescein conjugate can be administered to the patient at an interval of days or months after the initial injections(s) and the additional injections can prevent recurrence of disease. Alternatively, the initial injection(s) of the isolated ligand-fluorescein conjugate may prevent recurrence of disease.

Illustratively, the therapeutic factor can be administered to the host animal prior to, after, or at the same time as the isolated ligand-fluorescein conjugate and the therapeutic factor can be administered as part of the same composition containing the conjugate or as part of a different composition than the isolated ligand-fluorescein conjugate. Any such therapeutic composition containing the therapeutic factor at a therapeutically effective dose can be used in the present method. Additionally, more than one type of isolated ligand-fluorescein conjugate can be used. For example, a pteroic acid-fluorescein conjugate and a riboflavin-fluorescein conjugate can be used in combination. In the case of chemotherapeutic and antimicrobial agents, the therapeutic factor can be administered at a suboptimal dose along with the isolated ligand-fluorescein conjugate in a combination therapy to avoid development of resistance to the chemotherapeutic or antimicrobial agent by the host animal.

Illustratively, the isolated ligand-fluorescein conjugate and the therapeutic factor can be injected parenterally and such injections can be intraperitoneal injections, subcutaneous injections, intramuscular injections, intravenous injections or intrathecal injections. The isolated ligand-fluorescein conjugate and the therapeutic factor can also be delivered using a slow pump. Examples of parenteral dosage forms include aqueous solutions of the active agent, in an isotonic saline, 5% glucose or other well-known pharmaceutically acceptable liquid carriers such as liquid alcohols, glycols, esters, and amides. The parenteral dosage form can be in the form of a reconstitutable lyophilizate comprising the dose of isolated ligand-fluorescein conjugate and therapeutic factor. In one aspect of the present embodiment, any of a number of prolonged release dosage forms known in the art can be administered such as, for example, the biodegradable carbohydrate matrices described in U.S. Pat. Nos. 4,713,249; 5,266,333; and 5,417,982, the disclosures of which are incorporated herein by reference.

In another illustrative embodiment, pharmaceutical compositions are provided comprising an amount of an isolated carrier-fluorescein conjugate effective to establish a novel immunity to the fluorescein moiety in the conjugate when the host animal is preimmunized with the carrier-fluorescein conjugate. The carrier-fluorescein conjugate can be used in any of the dosages or dosage forms described above and can be administered according to any of the regimens described above.

EXAMPLES

Unless otherwise noted, all reactions were performed at ambient temperature; all evaporations were performed under reduced pressure or in vacuo; and Example compounds were analyzed by $^1$H NMR, $^{13}$C NMR, elemental analysis, analytical HPLC, UV absorption, and/or fluorescence, as appropriate.

Example 1

Synthesis of Compound 8a from a Pteroylglutamate

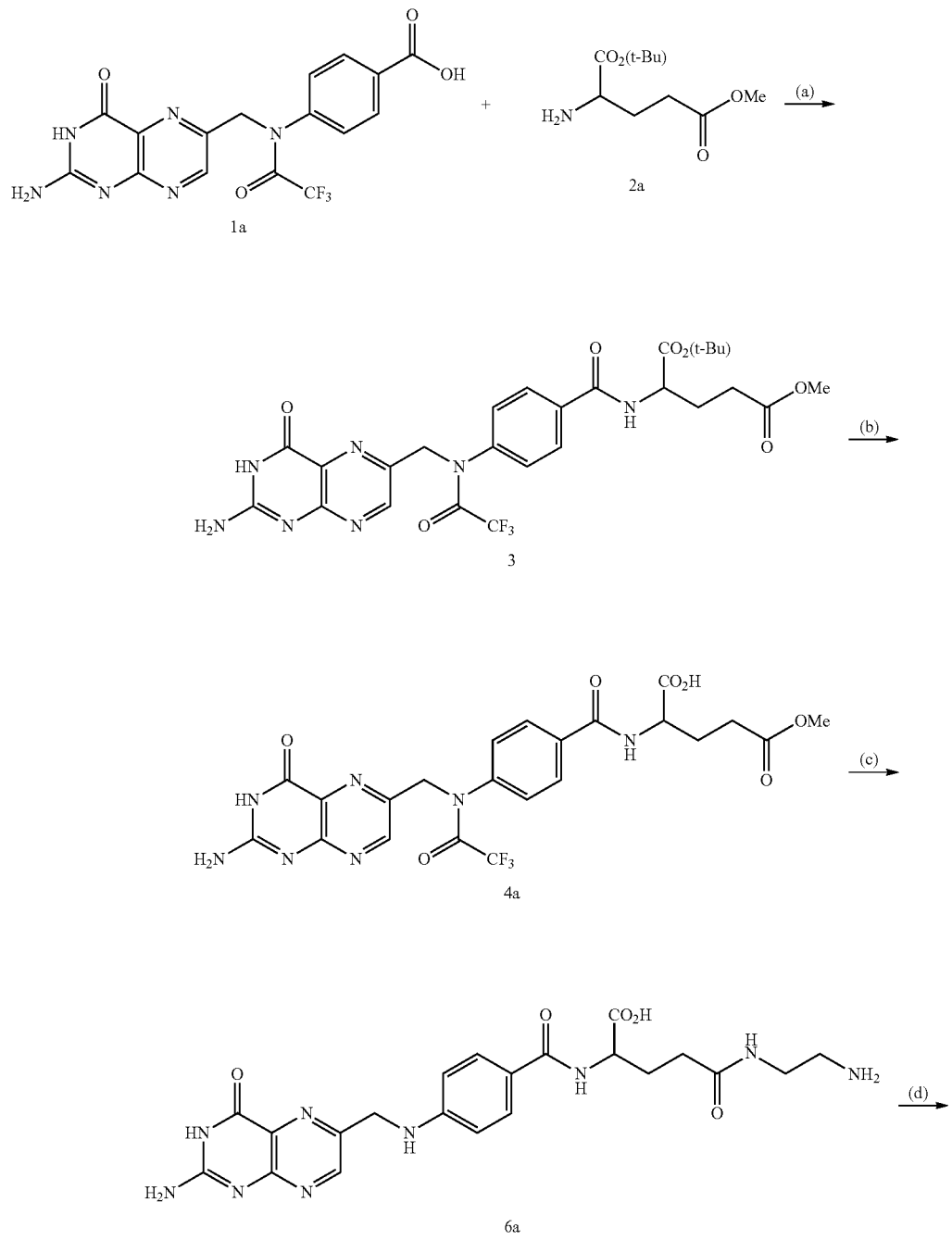

Scheme 4

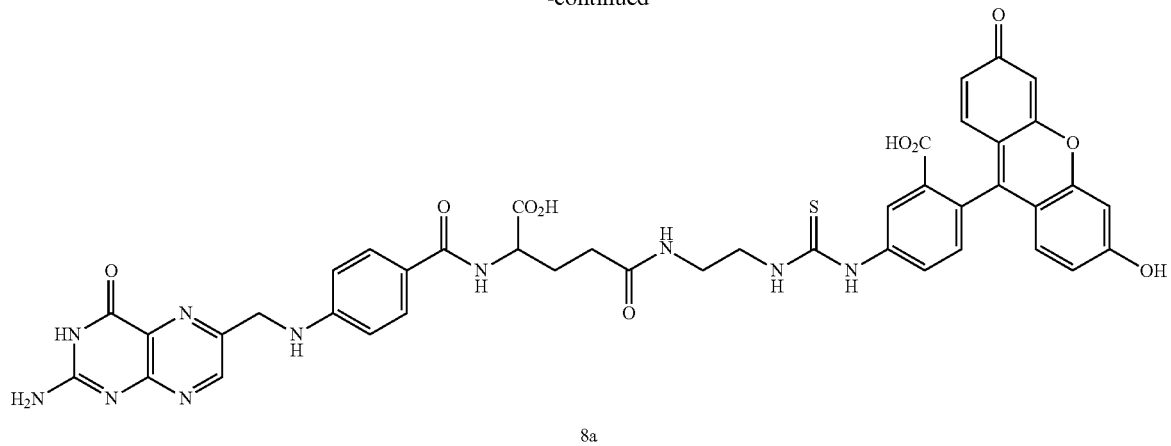

8a

Step (a). A solution of $N^{10}$-protected pteroic acid 1a (119 g, 0.25 mol) and the α-tert-butyl, γ-methyl diester of glutamate (2a, 76 g, 0.30 mol) in DMF (4 L) was treated with PyBop (171 g, 0.325 mol) and DIPEA (109 mL, 0.60 mol). After 18 h, the mixture was evaporated giving diester 3a as a precipitate from 1:1 ACN/methyl tert-butyl ether (MTBE).

Step (b). The tert-butyl protecting group of diester 3a was chemoselectively removed with 1:1 TFA/anhydrous DCM in the presence of poly(4-vinylpyridine) to give the α-acid, γ-methyl ester analog 4a as a precipitate from 1:1 petroleum ether/MTBE.

Step (c). A mixture of the α-acid, γ-methyl ester analog 4a and ethylene diamine (5a) was stirred for 2 h to form EDA-folate analog 6a. The $N^{10}$-trifluoroacetamide protecting group was simultaneously removed during the reaction. Compound 6a may be optionally purified to remove remaining ethylene diamine (5a) by column chromatography using a DEAE-cellulose solid support, such as DE52 (Whatman Cat. No. 4057-200).

Step (d). EDA-folate analog 6a was condensed with fluorescein isothiocyanate (FITC, 7) in the presence of DIPEA and 1,1,3,3-tetramethylguanidine (TMG) in DMSO, giving 8a (218 g), which was collected as a precipitate from 1:1 ACN/MTBE. Folate-FITC 8a was purified by reverse phase column chromatography (Biotage C18 cartridge, 100 mM sodium phosphate buffer/acetonitrile as mobile phase). Fractions containing 8a were detected by UV absorption (280 nm) and pooled. Volatile solvents were evaporated, and the residue was desalted by reverse phase column chromatography (Biotage C18 cartridge, water/acetonitrile as mobile phase). Volatile solvents were evaporated, and the residue was lyophilized to give 47 g (22% overall) of 8a. HPLC (Nova-Pak C18 column, 10 mM ammonium acetate/acetonitrile as mobile phase) indicated that the material was greater than 98% pure, and bisfluorescein derivative IIIa (n=1) was not detectable by UV or fluorescence.

Example 2

Synthesis of 8a from a Glutamylethylenediamine

Scheme 5

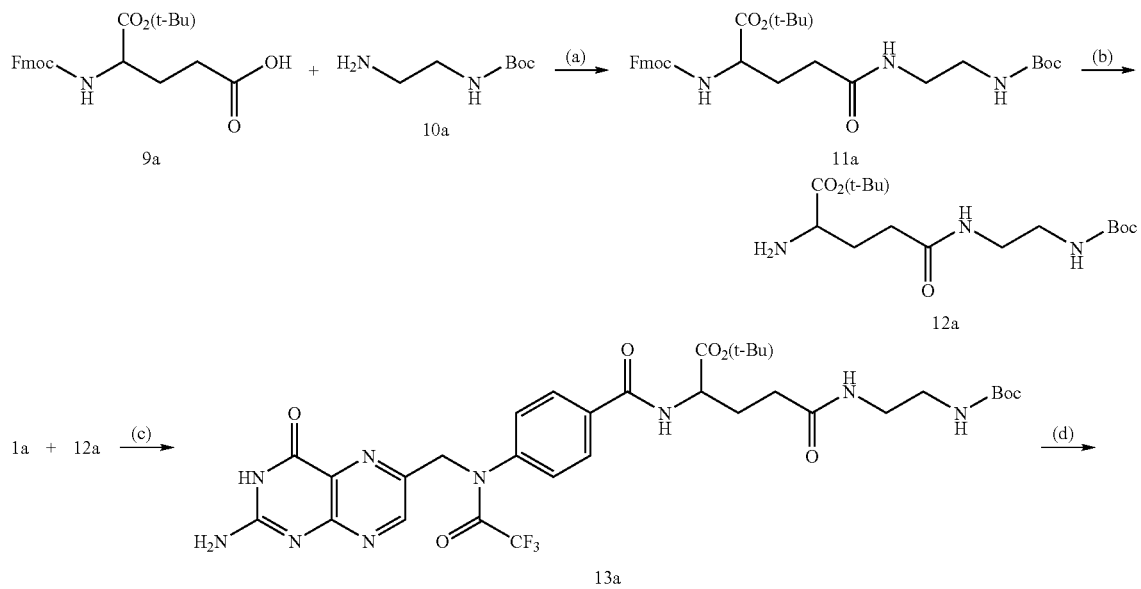

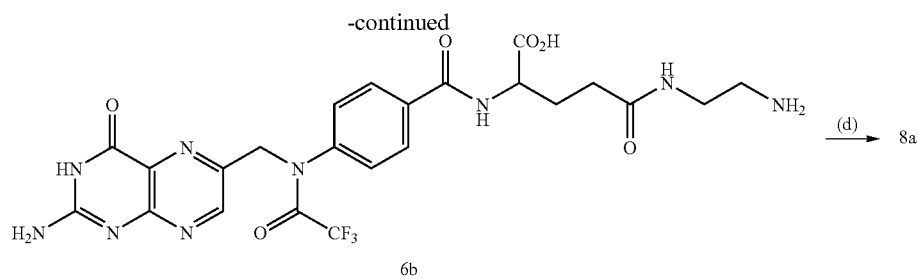

6b

Step (a). A mixture of protected glutamic acid 9a and protected ethylenediamine 10a in THF was treated with PyBOP and diisopropylethylamine (DIPEA). Amide 11a was isolated by extracting the reaction mixture with EtOAc. The combined organic phase was evaporated to give amide 11a.

Step (b). Amide 11a was treated with diazabicycloundecane (DBU) in methylene chloride at ambient temperature to remove the Fmoc protecting group. The mixture was evaporated to give amine 12a, which may be optionally purified. Alternatively as indicated below, steps (b)-(d) may be performed in a single operation without purification in a one-pot process.

Step (c). The residue from step (b), or optionally the purified form containing amine 12a, was dissolved in DMF and coupled with $N^{10}$-trifluoroacetylpteroic acid (1a) using PyBOP and DIPEA. The reaction mixture was evaporated to give folate analog 13a, which may be optionally purified. Alternatively as indicated below, steps (c)-(d) may be performed in a single operation without purification in a one-pot process.

Step (d). The residue from step (c), or optionally the purified form containing folate analog 13a, was dissolved in methylene chloride and treated with trifluoroacetic acid (TFA) and poly(4-vinylpyridine) as a cation scavenger to simultaneously remove the Boc and tert-butyl protecting groups. Double precipitation (butyl t-butyl ether, then 1:1 methyl t-butyl ether/$CH_3CN$) gave amine 6b as a light yellow solid.

Step (e). Condensation of amine 6b with fluorescein isothiocyanate (7) gave the corresponding $N^{10}$-trifluoroacetamide protected analog of 8a, which was collected as a precipitate. The precipitate was dissolved in water and the pH was raised to about 10 or greater resulting in hydrolysis of the $N^{10}$-trifluoroacetyl-protecting group, giving 8a.

Folate-FITC 8a was purified by reverse phase HPLC (XTerra column, 90:10 10 mM sodium phosphate buffer/ acetonitrile as mobile phase). Fractions containing 8a were detected by UV absorption (280 μm) and pooled. Volatile solvents were evaporated. The residue was desalted by reverse phase HPLC (XTerra column, 50:50 water/acetonitrile as mobile phase). Volatile solvents were evaporated, and the residue was lyophilized to give of 8a as an orange solid.

Example 3

Synthesis of 8a from a Ethylenediamineisothiocyanate

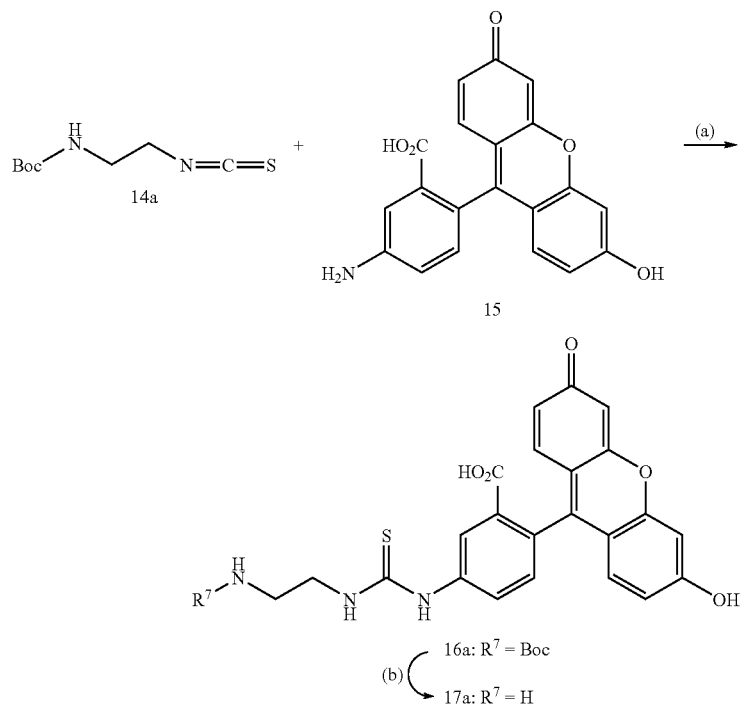

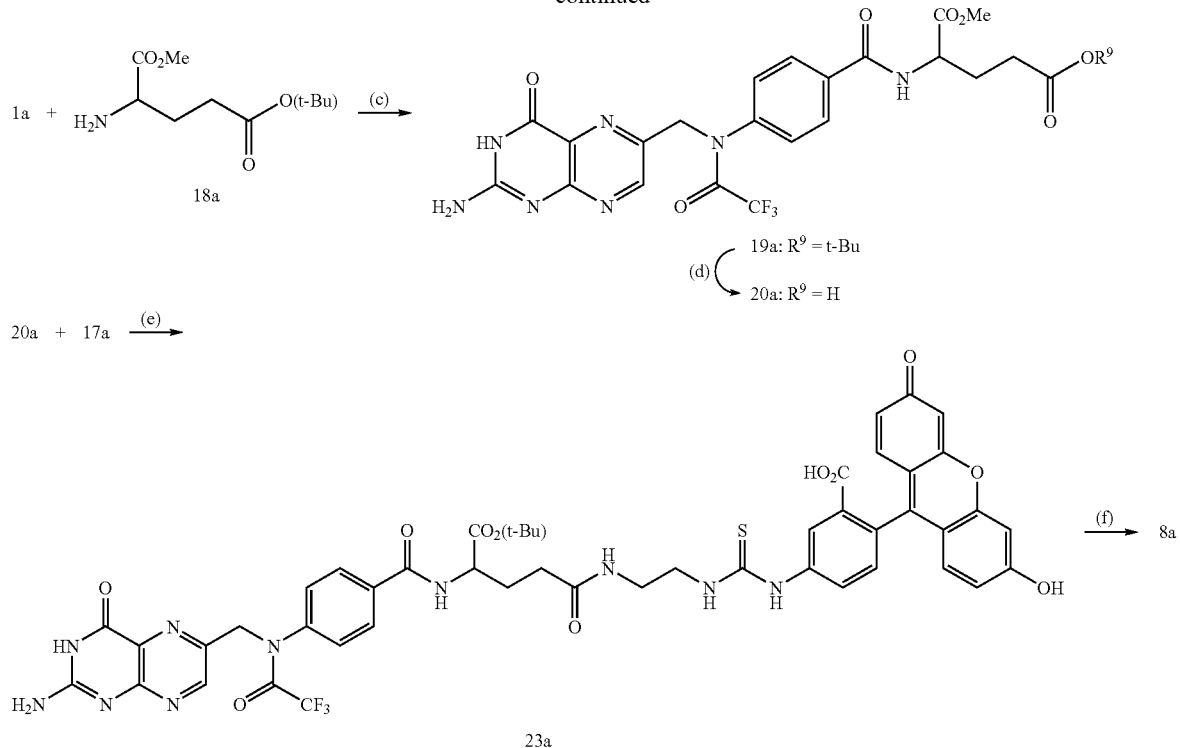

Step (a). A mixture of Boc-protected aminoethylisothiocyanate (14a, 1.5 mmol) and fluoresceinamine (15, Isomer-I, 0.3 mmol) in EtOH was heated at reflux for 24 h. The EtOH solvent was evaporated, the residue was dissolved in water, resulting in a pH of about 10. The aqueous layer was washed with EtOAc, and the pH of the aqueous layer was adjusted to 4.0 by addition of acid, resulting in Boc-protected amine 16a as a precipitate, which was freeze dried (70% yield).

Step (b). Boc-protected amine 16a was suspended in dry $CH_2Cl_2$, poly-(4-vinylpyridine) was added, then trifluoroacetic acid was slowly added. The resulting clear yellow solution was stirred for 3 h. The reaction mixture was filtered and precipitated with 1:1 methyl t-butyl ether (MTBE)/$CH_2Cl_2$. The precipitate was washed with MTBE and dried under high vacuum giving amine 17a in quantitative yield.

Step (c). PyBop (1.01 mmol) and glutamic acid (O-t-Bu) OMe (1.01 mmol) were sequentially added to a suspension of $N^{10}$-TFA-pteroic acid (0.84 mmol) in DMF. The resulting clear solution was treated with diisopropylethyl amine (DIPEA, 2.02 rmolM) and stirred for 3 h. The DMF was removed under reduced pressure and impure 19a was precipitated with 1:1 $CH_3CN$/MTBE. The precipitate was washed with 1:1 $CH_3CN$/MTBE and dried under high vacuum giving 19a in quantitative yield.

Step (d). Compound 19a was suspended in dry $CH_2Cl_2$ and poly-(4-vinylpyridine) and trifluoroacetic acid were added sequentially. The resulting clear yellow solution was stirred for 2 h, filtered, and impure 20a was precipitated with 1:1 MTBE/$CH_2Cl_2$. The precipitate was washed with MTBE and dried under high vacuum giving 20a (66% yield).

Step (e). PyBop (0.052 mmol) and DIPEA (0.20 mmol) were added simultaneously to a solution of folic acid analog 20a (0.05 mmol) and EDA-fluorescein 17a (0.05 mmol) in dry DMF. The resulting solution was stirred for 2 h, and impure 23a was precipitated with MTBE. The precipitate was washed with MTBE and dried under high vacuum giving 23a in quantitative yield.

Step (f). Compound 23a (0.05 mmol) was treated with an ice-cold solution of 0.5 M $Na_2CO_3$ (pH=10.6). The resulting bright orange solution was stirred for 4 h, followed by adjusting the reaction mixture pH to about 7.6-7.8 by addition of 1 M HCl. Purification by preparative HPLC column (eluent: 5.0 mM sodium phosphate/ACN) gave pure fractions containing compound 8a. ACN was removed under reduced pressure the concentrate was freeze dried to obtain 8a as an orange powder (60% yield).

Example 4

Pretreatment of DEAE Cellulose Anion Exchange Solid Support

Prior to loading the DEAE cellulose anion exchange solid support (for example DE32) onto a column, the solid support was slurried into 15 volumes of a 0.5 M HCl solution. After about 0.5 hours, the supernatant was decanted away, and the solid support was washed with water until the wash had a pH of about 4. The solid support was slurried into 15 volumes of a 0.5 M NaOH solution. After about 0.5 hours, the supernatant was decanted away, and the solid support was washed with water until the wash had a pH of about 8.

Example 5

Purification of Pteroic Acid from Folic Acid with DE32

Figure 1B:
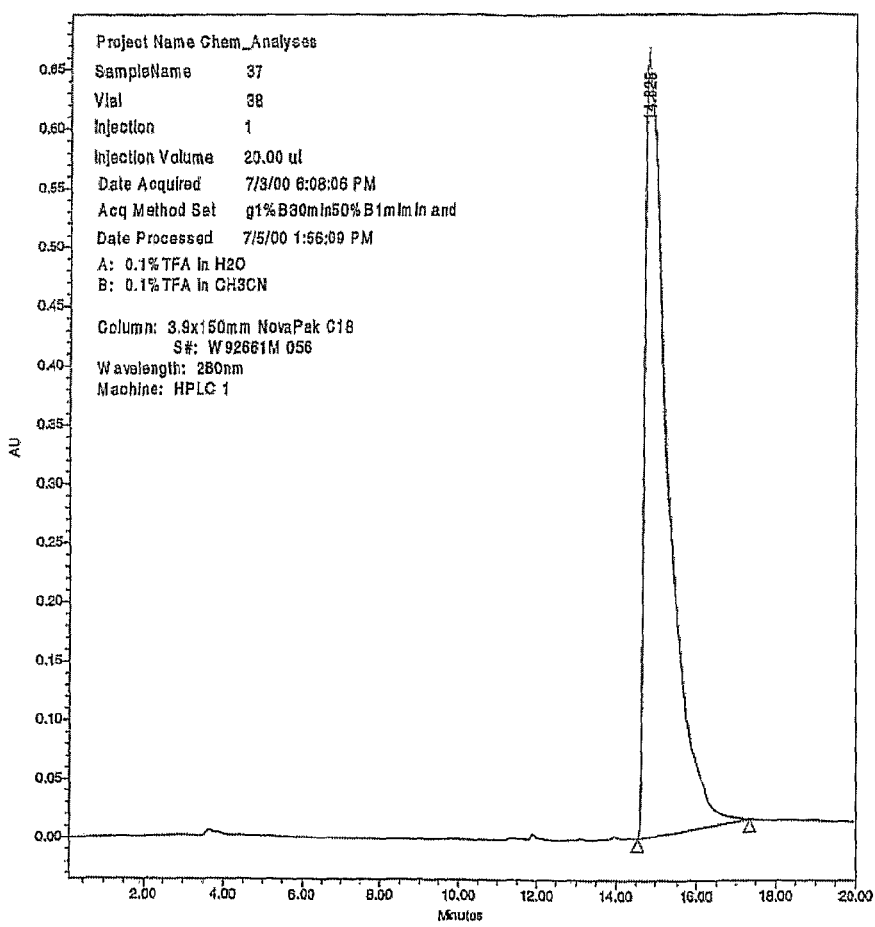
FIG. 1B shows the C18 reverse phase HPLC trace of fraction 38 eluted from a DEAE cellulose column (DE32) in the purification of pteroic acid.

Dry microgranular DE32 anion exchange resin (DEAE cellulose, Whatman Cat. No. 6055-010) was pretreated as described in Example 4. A slurry of the pretreated resin in deionized water was degassed for at least 1 hour under vacuum, uniformly packed into a glass column (25×900 mm), and the column was checked to minimize trapped bubbles. The column was equilibrated with the mobile phase (1.0 M NaCl/0.01 M NaOH, pH 11.5). A mixture containing pteroic acid and folic acid (1.0 g) was partially dissolved in 1.0 M NaCl (1 mL) at about pH 6. The mixture completely dissolved after adjusting the pH to 11.5. The resulting solution was loaded onto the column and eluted with the mobile phase (1.0 M NaCl/0.01 M NaOH). Referring to FIG. 1A, elution was monitored by UV absorption (280 nm). It was determined that folic acid eluted in fractions 13-31, and pteroic acid eluted in fractions 35-81. Referring to FIG. 1B, each of fractions 35-75 contained pteroic acid (greater than 99% pure) as determined by reversed phase HPLC on a Nova-Pak C18, 3.9×150 mm column running a 99:1 to 1:1 A/B gradient at 1 mL/min where A is a 0.1% TFA-$H_2O$ solution and B is a 0.1% TFA-$CH_3CN$ solution, with detection at 280 µm. Fractions 35-75 were combined, and the pH of the combined fraction was adjusted to about 2 by adding 1.0 M HCl. The resulting precipitate slurry was centrifuged, and the supernatant was decanted. The residue was resuspended in water, centrifuged, and the supernatant decanted (3 times). The residue was lyophilized to give 0.40 g of pteroic acid.

Example 6

Purification of Pteroic Acid from Folic Acid with DE52

Pre-swollen micro granular DE52 anion exchange resin (DEAE cellulose, Whatman Cat. No. 4057-200, 6 kg) was mixed with deionized water (12 L). The resulting slurry was degassed for at least 1 hour under vacuum, uniformly packed into a glass column (100×1200 mm), and the column was checked to minimize trapped bubbles. The column was equilibrated with the mobile phase (1.0 M NaCl, 0.01 M NaOH, pH 11.5). A sample of crude pteroic acid (40 g) containing about 25% folic acid was dissolved in water (500 mL), and the pH was adjusted to 11.5 by adding a NaOH solution. The solution was filtered, loaded onto the column, and eluted with the mobile phase. Each fraction was monitored by reversed phase HPLC. The fractions containing pteroic acid in greater than about 95% purity were combined, and the pteroic acid was precipitated from the combined fractions by adjusting the pH to about 3 by adding a 1.0 M HCl solution. The precipitate was lyophilized to give pteroic acid (20 g, >98% purity as determined by analytical reverse phase HPLC).

The column was regenerated by eluting 2 bed volumes of the mobile phase. Columns that were stored for about a week or longer were treated with a preservative, such as a 0.2% benzalkonium chloride solution.

Example 7

Purification of a Folate-Fluorescein Conjugate from Fluorescein

Pre-swollen micro granular DE52 anion resin (DEAE cellulose, Whatman Cat. No. 4057-200, 1.8 kg) was pretreated as described in Example 6. A slurry of the pretreated resin in deionized water (4 L) was degassed for at least 1 hour under vacuum, uniformly packed into a glass column (75×600 mm), and the column was checked to minimize trapped bubbles. The column was equilibrated with the mobile phase (1.0 M NaCl, NaOH to pH 9.0). A sample of crude folate-fluorescein conjugate (47.9 g) containing about 10% fluorescein and other impurities was dissolved in water (600 mL), and the pH was adjusted to 9.0 by adding a 1.0 M NaOH solution. The solution was filtered, loaded onto the column, and eluted with the mobile phase. Each fraction was monitored by reversed phase HPLC. The fractions containing folate-fluorescein conjugate in greater than about 95% purity were combined, and the folate-fluorescein conjugate was precipitated from the combined fractions by adjusting the pH to about 3 by adding a 1.0 M HCl solution. The precipitates was lyophilized to give 8a (41.8 g).

Example 8

Purification of 8a by HPLC

A sample of impure 8a (4 g) was prepared as described in Example 1 and purified by preparative HPLC using an XTERRA RP18, 30×300 mm 10 µm column (Waters) running a 100:0 to 91:9 A/B gradient over 30 min at 35 ml/min (where A was a 100 mM sodium phosphate (pH 7.4) solution and B was ACN). Compound 8a eluted and was collected in fractions, while the bisfluorescein-derivative did not elute under these conditions and was not detected. Each eluted fraction was monitored by analytical reverse phase HPLC with both a UV detector and a fluorescence detector. Fractions that were greater than 98% purity by UV, did not contain any EDA-bisfluorescein or bisfluorescein impurities by UV or by fluorescence (threshold of less than 0.1%) were combined. The ACN was evaporated at a temperature less than about 35° C. The column was regenerated by eluting 1:1 A/B for two or more bed volumes.

The resulting solution of 8a containing phosphate salts was purified by reverse phase HPLC on a column equilibrated with 100% water for injection (WFI) by eluting with WFI for 30 min to wash out the phosphate salts, followed by a 100:0 to 91:9 WFI/ACN gradient over 30 min at 35 mL/min to elute 8a. Each fraction was also monitored by analytical reverse phase HPLC with both a UV detector and a fluorescence detector. Fractions with greater than 98% purity by UV and less than 0.05% EDA-bisfluorescein or bisfluorescein impurities by fluorescence were pooled and lyophilized to obtain 8a as a powder.

Example 9

Effect of Isolated Folate-Fluorescein Conjugates on Growth of Solid Tumors

Figure 2:
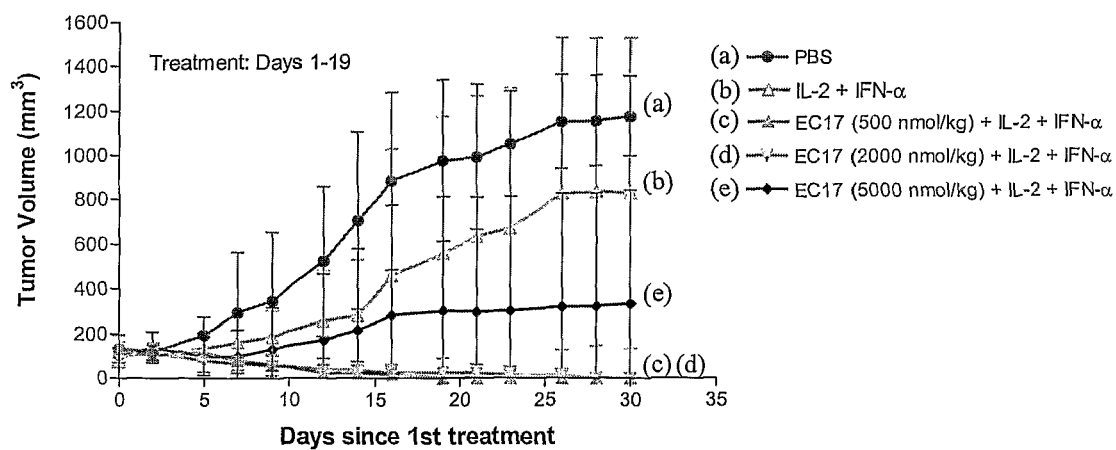
FIG. 2 shows the effect of isolated folate-fluorescein conjugates on the growth of solid tumors.

Six to eight-week old (~20-22 grams) female Balb/c mice (8 mice/group) were immunized subcutaneously at multiple sites with fluorescein-labeled keyhole limpet hemocyanin (KLH) using a commercial saponin adjuvant (GPI-0100; Galenica). After assuring that anti-fluorescein antibody titers were high in all mice (as evidenced by the results of ELISA assays of serum samples of the mice), each animal was injected subcutaneously in the shoulder with $1\times10^6$ M109 cells (a syngeneic lung cancer cell line that expresses high levels of the folate receptor; day 0) following prior immunization with KLH-fluorescein. The immunizations with folate-fluorescein after tumor cell implantation consisted of 500, 2000, or 5000 nmol/kg of folate-fluorescein, conjugated via a gamma carboxyl-linked ethylene diamine bridge, given in 19 intraperitoneal doses at 24 hour intervals (days 1-19). Control animals were injected with phosphate buffered saline (PBS). A series of 5 daily injections (five times a week) for three weeks of 20,000 IU/day of recombinant human IL-2 were administered to all mice in order to stimulate the immune system. A series of 3 injections for three weeks of 25,000 U/day of recombinant human IFN-α were also administered to all mice. The efficacy of this immunotherapy was then evaluated by monitoring tumor volume ($mm^3$) using a caliper. The tumor growth curves depicted in FIG. 2 show that the growth of solid tumors was significantly inhibited when animals were treated with folate-fluorescein in combination with IL-2 and IFN-α.

Example 10

Purification of EDA-Folate (6a) with DE52

Pre-swollen microgranular DE52 anion exchange resin (DEAE cellulose, SIGMA) was mixed with deionized water (12 L). The slurry was degassed for at least 1 h under vacuum, uniformly packed into a glass column (100×1200 mm), and the column was checked to minimize trapped bubbles. The column was equilibrated with a NaOH solution at pH 10.5. A sample of EDA-folate 6a contaminated with ethylene diamine 5a was partially dissolved in water at neutral pH, and completely dissolved after adjusting the solution to pH 10.5 by adding a NaOH solution. After loading the pH adjusted solution, the column was first eluted with 3 bed volumes of NaOH solution at pH 10.5, and then eluted with 2 bed volumes of 1.0 M NaCl/NaOH solution (pH 10.5). The yellow colored fractions obtained while eluting with 1.0 M NaCl/NaOH (pH 10.5) solution were collected and combined. EDA-folate 6a was precipitated from the pooled fractions by adjusting the pH to about 7 by adding an HCl solution. After freeze drying, a small portion of 6a was coupled with fluorescein and analyzed by HPLC with a fluorescence detector. EDA-bisfluorescein compounds of formulae II and III were not detected.

Example 11

Purification of Compound 8a as a Calcium or Magnesium Salt

Treatment of 8a as a sodium salt (84% purity) with 10-50 mol equivalents of magnesium chloride or calcium chloride in water resulted in precipitation. After heating the mixture to 90-100° C., the precipitate dissolved to give a yellow solution, which was filtered, and slowly cooled to room temperature. The resulting yellow solids were filtered, washed with water, and freeze dried to give 8a in 93-97% purity. The calcium or magnesium salt may be converted to the sodium salt by ion exchange.

The invention claimed is:

1. A method for purifying pteroic acid, a derivative of pteroic acid, an analog of pteroic acid, or a combination thereof, the method comprising the steps of:
   (a) contacting a solution comprising pteroic acid, the derivative of pteroic acid, the analog of pteroic acid, or the combination thereof with an ion exchange chromatographic support;
   (b) eluting a first fraction comprising pteroic acid, the derivative of pteroic acid, or the analog of pteroic acid, with a mobile phase having a pH of about 10 or greater; and
   (c) lowering the pH of the first fraction to about 3 or less to form a precipitate of pteroic acid, the derivative of pteroic acid, or the analog of pteroic acid.

2. The method of claim 1 wherein the ion exchange chromatographic support comprises a saccharide-based ion exchange resin.

3. The method of claim 1 wherein the ion exchange chromatographic support comprises a saccharide-based anion exchange resin.

4. The method of claim 1 wherein the ion exchange chromatographic support comprises a saccharide-based anion exchange resin comprising cellulose, amylose, or a combination thereof.

5. The method of claim 1 wherein the ion exchange chromatographic support comprises a saccharide-based anion exchange resin selected from the group consisting of diethylaminoethyl cross-linked dextran, quaternary amine cross-linked dextran, polyethyleneimine cellulose quaternary amine cellulose, diethylaminoethyl cellulose, and combinations thereof.

6. The method of claim 1 wherein the solution further comprises folic acid, a derivative of folic acid, or a combination thereof.

7. The method of claim 6 further comprising the step of (e) eluting a second fraction comprising folic acid or the derivative of folic acid, where the first fraction is substantially separated from the second fraction.

8. The method of claim 6 wherein the ion exchange chromatographic support comprises a saccharide-based anion exchange resin selected from the group consisting of diethylaminoethyl cross-linked dextran, quaternary amine cross-linked dextran, polyethyleneimine cellulose, quaternary amine cellulose, diethylaminoethyl cellulose, and combinations thereof.

9. The method of claim 1 wherein the mobile phase has a pH of about 11 or greater.

10. The method of claim 1 wherein the mobile phase has a pH in the range from about 11 to about 13.

11. The method of claim 1 wherein the mobile phase is substantially free of ammonia or salts thereof.

12. The method of claim 1 wherein the precipitate has a purity of about 95% by weight or greater.

13. The method of claim 1 wherein the precipitate has a purity of about 98% by weight or greater.

14. The method of claim 1 wherein the precipitate has a purity of about 99% by weight or greater.

15. The method of claim 1 wherein the precipitate is substantially free of folic acid.

16. The method of claim 1 wherein the pteroic acid derivative is of the formula

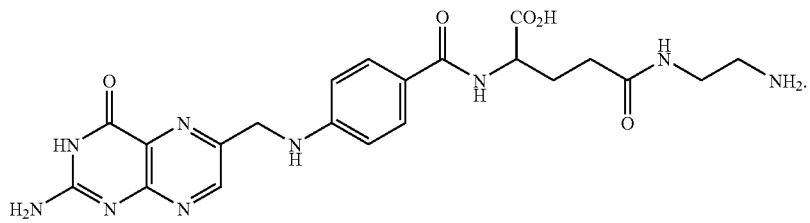

17. A method for purifying pteroic acid, a derivative of pteroic acid, an analog of pteroic acid, or a combination thereof, the method comprising the steps of:
   (a) contacting a solution comprising pteroic acid, the derivative of pteroic acid, the analog of pteroic acid, or the combination thereof with an anion exchange chromatographic support selected from the group consisting of diethylaminoethyl cross-linked dextran, quaternary amine cross-linked dextran, polyethyleneimine cellulose, quaternary amine cellulose, diethylaminoethyl cellulose, and combinations thereof; and
   (b) eluting a first fraction comprising pteroic acid, the derivative of pteroic acid, or the analog of pteroic acid.

18. A method for purifying a conjugate comprising pteroic acid, a derivative thereof, or an analog of pteroic acid, and fluorescein or a derivative of fluorescein, the method comprising the steps of:
   (a) contacting a solution comprising the conjugate with a first reversed phase chromatographic support;
   (b) eluting from the first reversed phase chromatographic support a fraction comprising a phosphate complex of the conjugate with a mobile phase, said mobile phase comprising a phosphate salt and having a pH in the range from about 6 to about 8;
   (c) contacting a solution of the phosphate complex of the conjugate with a second reversed phase chromatographic support; and
   (d) eluting from the second reversed phase chromatographic support a fraction comprising the conjugate with a mobile phase comprising water, where the fraction comprising the conjugate is substantially free of phosphate.

19. The method of claim 18 wherein the conjugate is a compound of the formula

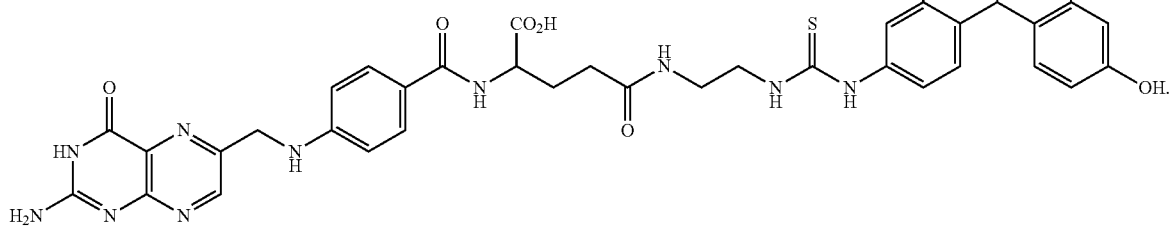

20. The method of claim 18 wherein the mobile phase further comprises acetonitrile in eluting step (b) and eluting step (d).

21. The method of claim 1 wherein the derivative of pteroic acid is of the formula

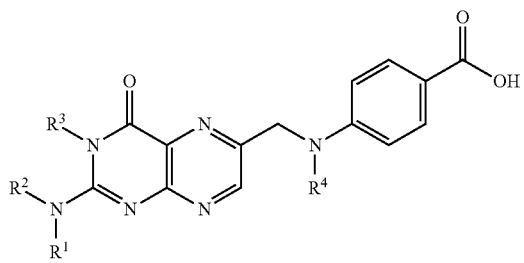

wherein $R^1$, $R^2$, $R^3$ and $R^4$ are each independently selected from the group consisting of hydrogen, alky, acyl, and nitrogen protecting group, or $R^1$ and $R^2$ are taken together to form a nitrogen protecting group.

* * * * *